United States Patent
Mansi et al.

(10) Patent No.: US 10,902,602 B1
(45) Date of Patent: Jan. 26, 2021

(54) METHOD AND SYSTEM FOR COMPUTER-AIDED TRIAGE OF STROKE

(71) Applicant: Viz.ai Inc., San Francisco, CA (US)

(72) Inventors: Christopher Mansi, San Francisco, CA (US); David Golan, San Francisco, CA (US); Gil Levi, San Francisco, CA (US); Yuval Duchin, San Francisco, CA (US)

(73) Assignee: Viz.ai Inc., San Francisco, CA (US)

( * ) Notice: Subject to any disclaimer, the term of this patent is extended or adjusted under 35 U.S.C. 154(b) by 0 days.

(21) Appl. No.: 16/938,598

(22) Filed: Jul. 24, 2020

Related U.S. Application Data

(60) Provisional application No. 62/880,227, filed on Jul. 30, 2019.

(51) Int. Cl.
| | |
|---|---|
| *A61B 5/00* | (2006.01) |
| *G16H 10/20* | (2018.01) |
| *G06T 7/00* | (2017.01) |
| *G06T 7/11* | (2017.01) |
| *G06T 5/50* | (2006.01) |

(52) U.S. Cl.
CPC .............. *G06T 7/11* (2017.01); *A61B 5/7264* (2013.01); *G06T 5/50* (2013.01); *G06T 7/0012* (2013.01); *G16H 10/20* (2018.01); *G06T 2207/20084* (2013.01); *G06T 2207/30016* (2013.01)

(58) Field of Classification Search
CPC ........ A61B 5/7264; G16H 10/20; G06T 5/50; G06T 7/0012; G06T 7/11; G06T 2207/20084; G06T 2207/30016
See application file for complete search history.

(56) References Cited

U.S. PATENT DOCUMENTS

| | | | |
|---|---|---|---|
| 6,349,330 | B1 | 2/2002 | Bernadett et al. |
| 8,374,414 | B2 | 2/2013 | Tang et al. |
| 9,307,918 | B2 | 4/2016 | Kinrot et al. |
| 10,346,979 | B2 | 7/2019 | Mansi et al. |
| 10,373,315 | B2 | 8/2019 | Mansi et al. |
| 2006/0140473 | A1 | 6/2006 | Brooksby et al. |
| 2008/0021502 | A1 | 1/2008 | Imielinska et al. |
| 2009/0129649 | A1 | 5/2009 | Djeridane |
| 2009/0279752 | A1 | 11/2009 | Sirohey et al. |

(Continued)

FOREIGN PATENT DOCUMENTS

WO 2016134125 A1 8/2016

OTHER PUBLICATIONS

Yu et al. ("Use of Deep Learning to Predict Final Ischemic Stroke Lesions From Initial Magnetic Resonance Imaging," JAMA Network Open, Mar. 12, 2020) (Year: 2020).*

(Continued)

*Primary Examiner* — Yubin Hung
(74) *Attorney, Agent, or Firm* — Jeffrey Schox; Caitlin Ploch

(57) ABSTRACT

A system for computer-aided triage includes a router, a remote computing system, and a client application. A method for computer-aided triage includes receiving a data packet associated with a patient and taken at a point of care; checking for a suspected condition associated with the data packet; in an event that the suspected condition is detected, determining a recipient based on the suspected condition; and transmitting information to a device associated with the recipient.

20 Claims, 14 Drawing Sheets

(56) References Cited

U.S. PATENT DOCUMENTS

| | | | |
|---|---|---|---|
| 2010/0106002 A1* | 4/2010 | Sugiyama | G06T 9/20 600/410 |
| 2011/0116702 A1 | 5/2011 | Bredno et al. | |
| 2012/0065987 A1 | 3/2012 | Farooq et al. | |
| 2013/0185096 A1 | 7/2013 | Giusti et al. | |
| 2013/0208966 A1 | 8/2013 | Zhao et al. | |
| 2014/0142982 A1 | 5/2014 | Janssens | |
| 2014/0142983 A1 | 5/2014 | Backhaus et al. | |
| 2014/0222444 A1 | 8/2014 | Cerello et al. | |
| 2015/0011902 A1 | 1/2015 | Wang | |
| 2015/0104102 A1* | 4/2015 | Carreira | G06K 9/4676 382/195 |
| 2015/0208994 A1 | 7/2015 | Rapoport | |
| 2015/0320365 A1 | 11/2015 | Schulze et al. | |
| 2016/0037057 A1 | 2/2016 | Westin et al. | |
| 2016/0063191 A1 | 3/2016 | Vesto et al. | |
| 2016/0180042 A1 | 6/2016 | Menon et al. | |
| 2017/0143428 A1 | 5/2017 | Raffy et al. | |
| 2017/0147765 A1 | 5/2017 | Mehta | |
| 2017/0228516 A1 | 8/2017 | Sampath et al. | |
| 2017/0258433 A1 | 9/2017 | Gulsun et al. | |
| 2017/0300654 A1 | 10/2017 | Stein et al. | |
| 2017/0340260 A1 | 11/2017 | Chowdhury et al. | |
| 2018/0025255 A1* | 1/2018 | Poole | G06T 7/0014 382/131 |
| 2018/0085001 A1 | 3/2018 | Berger et al. | |
| 2018/0116620 A1 | 5/2018 | Chen et al. | |
| 2018/0235482 A1 | 8/2018 | Fonte et al. | |
| 2018/0253530 A1 | 9/2018 | Goldberg et al. | |
| 2018/0365824 A1 | 12/2018 | Yuh et al. | |
| 2018/0365828 A1 | 12/2018 | Mansi et al. | |
| 2018/0366225 A1 | 12/2018 | Mansi et al. | |
| 2019/0380643 A1 | 12/2019 | Kochura et al. | |
| 2020/0294241 A1* | 9/2020 | Wu | G06K 9/6256 |

OTHER PUBLICATIONS

Mittal et al. ("Fast Automatic Detection of Calcified Coronary Lesions in 3D Cardiac CT Images," International Workshop on Machine Learning in Medical Imaging, MLMI 2010) (Year: 2010).*

Kuang et al. ("Segmenting Hemorrhagic and Ischemic Infarct Simultaneously From Follow-Up Non-Contrast CT Images in Patients With Acute Ischemic Stroke," IEEE Access, vol. 7, Mar. 22, 2019) (Year: 2019).*

Lewis et al., "Ambulance smartphone tool—accuracy" BMJ, 2016, pp. 1-5 (Year: 2016).

Yu Y. et al., "Use of Deep Learning to Predict Final Ischemic Stroke Lesions From Initial Magnetic Resonance Imaging", Mar. 1, 2020, https://europepmc.org/article/med/32163165.

Kirisil, H.A., et al., "Standardized evaluation framework for evaluating coronary artery stenosis detection, stenosis quantification and lumen segmentation algorithms in computed tomography angiography", Elsevier, 2013, pp. 859-876.

Smith, Wade S., et al., "Prognostic Significance of Angiographically Confirmed Large Vessel Intracranial Occlusion in Patients Presenting With Acute Brain Ischemia", Neurocritical Care, vol. 4, 2006.

* cited by examiner

METHOD AND SYSTEM FOR COMPUTER-AIDED TRIAGE OF STROKE

CROSS-REFERENCE TO RELATED APPLICATIONS

This application claims the benefit of U.S. Provisional Application No. 62/880,227, filed 30 Jul. 2019, which is incorporated herein in its entirety by this reference.

TECHNICAL FIELD

This invention relates generally to the medical diagnostic field, and more specifically to a new and useful system and method for computer-aided triage in the medical diagnostic field.

BACKGROUND

In current triaging workflows, especially those in an emergency setting, a patient presents at a first point of care, where an assessment, such as imaging, is performed. The image data is then sent to a standard radiology workflow, which typically involves: images (equivalently referred to herein as instances) being uploaded to a radiologist's queue, the radiologist reviewing the images at a workstation, the radiologist generating a report, an emergency department doctor reviewing the radiologist's report, the emergency department doctor determining a specialist to contact, and making a decision of how to treat and/or transfer the patient to a $2^{nd}$ point of care. This workflow is typically very time-consuming, which increases the time it takes to treat and/or transfer a patient to a specialist. In many conditions, especially those involving stroke, time is extremely sensitive, as it is estimated that in the case of stroke, a patient loses about 1.9 million neurons per minute that the stroke is left untreated (Saver et al.). Further, as time passes, the amount and types of treatment options available to the patient decrease.

In some instances, such as that of brain tissue injury and/or death (e.g., ischemic core, ischemic penumbra, etc.), the time until treatment is particularly critical, not only because the brain tissue continues to experience greater injury/death as time passes, but because the particular treatment option can be highly dependent upon the amount of time that has passed, as this determines any or all of: an amount of affected brain, a severity of the affected brain, and a function of the affected brain.

Thus, there is a need in the triaging field to create an improved and useful system and method for decreasing the time it takes to determine a suspected condition and initiate treatment for the patient.

DESCRIPTION OF THE PREFERRED EMBODIMENTS

The following description of the preferred embodiments of the invention is not intended to limit the invention to these preferred embodiments, but rather to enable any person skilled in the art to make and use this invention.

1. Overview

Figure 1:
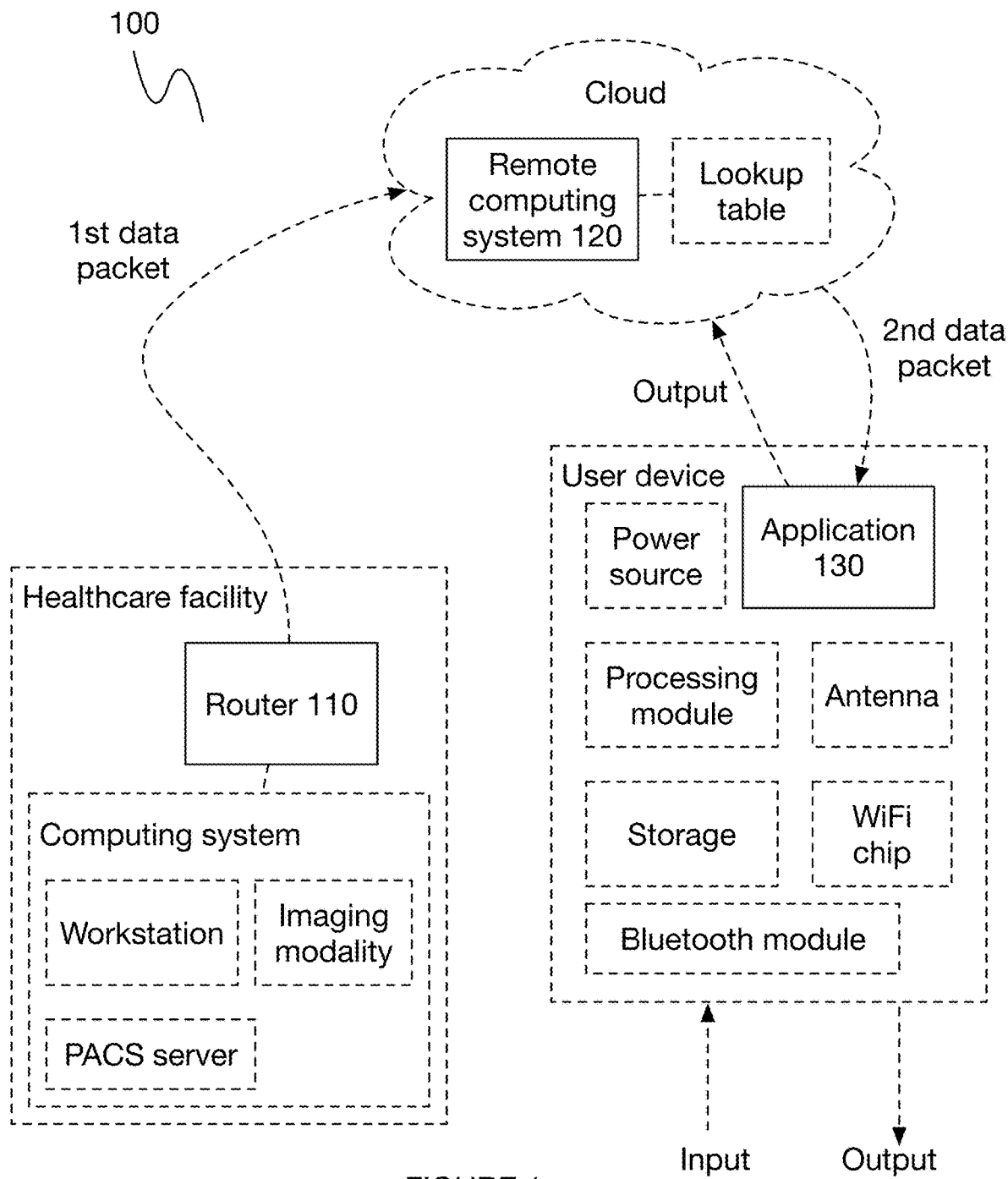
FIG. 1 is a schematic of a system for computer-aided triage.

As shown in FIG. 1, a system 100 for computer-aided triage includes a router, a remote computing system, and a client application. Additionally or alternatively, the system 100 can include any number of computing systems (e.g., local, remote), servers (e.g., PACS server), storage, lookup table, memory, and/or any other suitable components. Further additionally or alternatively, the system can include any or all of the components, embodiments, and examples as described in any or all of: U.S. application Ser. No. 16/012,458, filed 19 Jun. 2018; and U.S. application Ser. No. 16/012,495, filed 19 Jun. 2018; U.S. application Ser. No. 16/688,721, filed 19 Nov. 2019; and U.S. application Ser. No. 16/913,754, filed 26 Jun. 2020; each of which is incorporated in its entirety by this reference.

Figure 2:
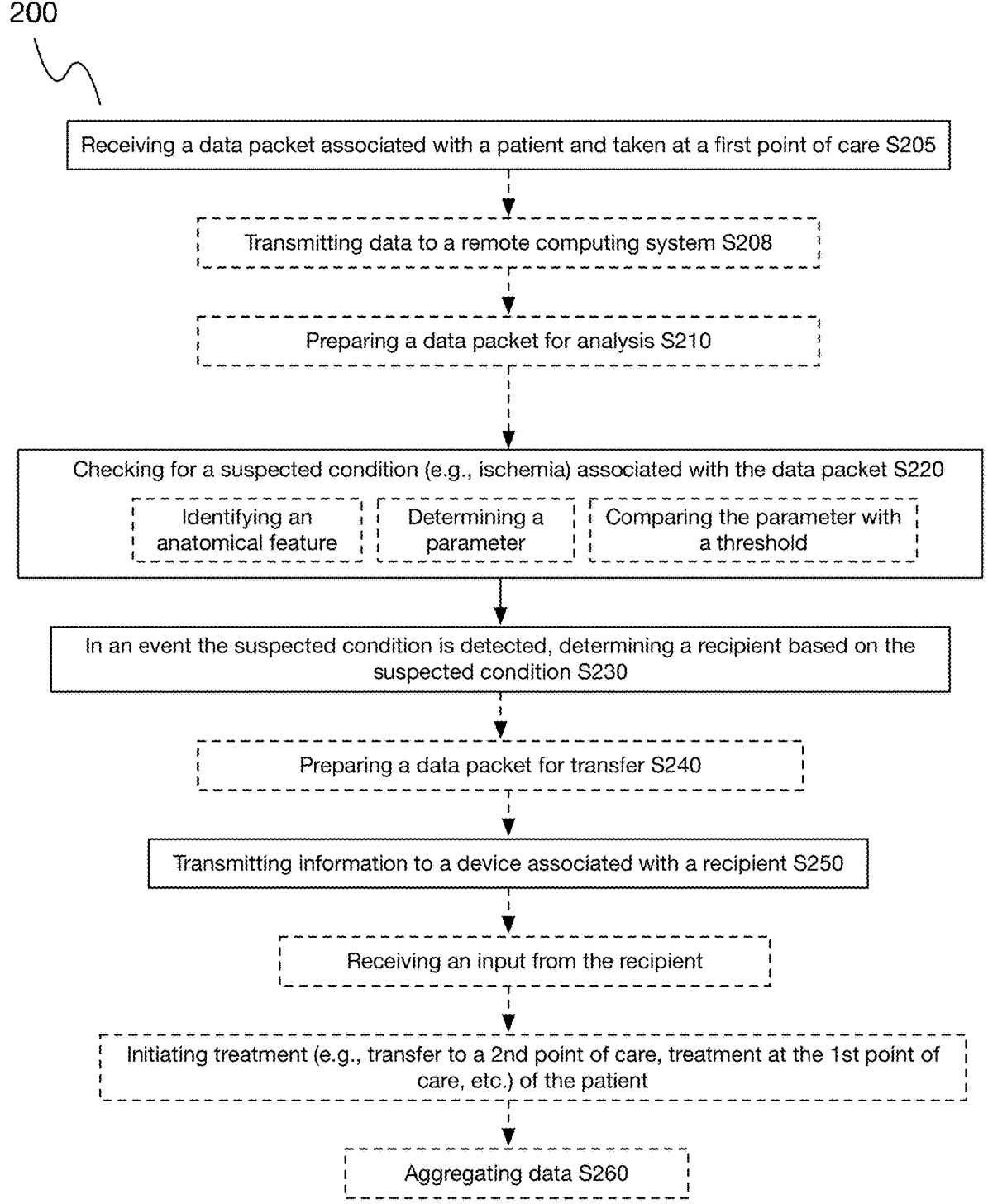
FIG. 2 is a schematic of a method for computer-aided triage.

As shown in FIG. 2, a method 200 for computer-aided triage includes receiving a data packet associated with a patient and taken at a first point of care S205; checking for a suspected condition associated with the data packet S220; in an event that the suspected condition is detected, determining a recipient based on the suspected condition S230; and transmitting information to a device associated with the recipient S250. Additionally or alternatively, the method 200 can include any or all of: transmitting data to a remote computing system S208; preparing a data packet for analysis S210; determining a parameter associated with a data packet; determining a treatment option based on the parameter; preparing a data packet for transfer S240; receiving an input from the recipient; initiating treatment of the patient; transmitting information to a device associated with a second point of care; aggregating data; and/or any other suitable processes. Further additionally or alternatively, the method 200 can include any or all of the processes, embodiments, and examples described in any or all of: U.S. application Ser. No. 16/012,458, filed 19 Jun. 2018; and U.S. application Ser. No. 16/012,495, filed 19 Jun. 2018; U.S. application Ser. No. 16/688,721, filed 19 Nov. 2019; and U.S. application Ser. No. 16/913,754, filed 26 Jun. 2020; each of which is incorporated in its entirety by this reference, or any other suitable processes performed in any suitable order. The method 200 can be performed with a system 100 as described above and/or any other suitable system.

2. Benefits

The system and method for computer-aided triage can confer several benefits over current systems and methods.

In a first variation, the system and/or method confers the benefit of reducing the time to match and/or transfer a patient presenting with a condition (e.g., ischemia, ischemic core, ischemic penumbra, ischemic stroke, etc.) to a specialist. In a specific example, for instance, the average time between generating a non-contrast dataset and notifying a specialist is reduced from over 50 minutes to less than 8 minutes.

In a second variation, additional or alternative to those described above, the system and/or method provides a parallel process to a traditional workflow (e.g., standard radiology workflow), which can confer the benefit of reducing the time to determine a treatment option while having the outcome of the traditional workflow as a backup in the case that an inconclusive or inaccurate determination (e.g., false negative, false positive, etc.) results from the method.

In a third variation, additional or alternative to those described above, the system and/or method is configured to have a high sensitivity (e.g., 87.8%, approximately 88%, between 81% and 93%, greater than 87%, etc.), which functions to detect a high number of true positive cases and help these patients reach treatment faster. In the event that this results in a false positive, only a minor disturbance—if any—is caused to a specialist, which affects the specialist's workflow negligibly (e.g., less than 5 minutes), if at all. In a specific example, the method is configured to have a sensitivity above a predetermined threshold after a particular category of artifacts (e.g., motion artifacts, metal artifacts, etc.) have been checked for.

In a fourth variation, additional or alternative to those described above, the system and/or method confers the benefit of minimizing the occurrence of false positive cases (e.g., less than 10% occurrence, less than 5% occurrence, less than, which functions to minimize disturbances caused to specialists or other individuals. This can function to minimize unnecessary disturbances to specialists in variations in which specialists or other users are notified on a mobile device upon detection of a potential brain condition (e.g., ischemic core), as it can minimize the occurrence of a specialist being alerted (e.g., potentially at inconvenient times of day, while the specialist is otherwise occupied, etc.) for false positives, while still maintaining a fallback in the standard radiology workflow in the event that a true positive is missed. In a set of specific examples, the method includes training (e.g., iteratively training) a set of deep learning models involved in ischemic condition detection on images originally detected to be a true positive but later identified as a false positive.

In a fifth variation, additional or alternative to those described above, the system and/or method confers the benefit of reorganizing a queue of patients, wherein patients having a certain condition are detected early and prioritized (e.g., moved to the front of the queue).

In a sixth variation, additional or alternative to those described above, the system and/or method confers the benefit of determining a patient condition (e.g., brain ischemia, ischemic core, ischemic penumbra, dead brain volume above a predetermined threshold, etc.) with a non-contrast (e.g., non-perfusion) scan. In a specific example, this determination is made in less time (e.g., after the non-contrast scan has been performed, in absence of a non-contrast scan, etc.) than it would take to perform and assess a contrast scan (e.g., CTP scan).

In a seventh variation, additional or alternative to those described above, the system and/or method confers the benefit of determining actionable analytics to optimize a workflow, such as an emergency room triage workflow.

In an eighth variation, additional or alternative to those described above, the system and/or method confers the benefit of determining (e.g., quantifying) an amount of brain that can potentially be saved (e.g., is uninjured, is reversibly injured, etc.), which can subsequently be used in future decision making (e.g., performing an operation only when a percentage of brain above a predetermined threshold can be saved and/or maintained). Additionally or alternatively, the method can function to determine which areas of the brain (e.g., functional regions, territories, lobes, etc.) can be saved (and/or are not able to saved), which can also be used in future decision making (e.g., anticipating and/or scheduling a particular rehabilitation, refraining from drastic intervention if a critical area of the brain has been damaged, etc.).

In a ninth variation, additional or alternative to those described above, the system and/or method confers the benefit of detecting a brain ischemic condition (e.g., ischemia, ischemic core, ischemic penumbra, ischemic stroke, etc.), which is conventionally hard to detect, especially in non-perfusion/non-contrast scans. In some examples, for instance, the method leverages a natural symmetry of the brain between the left and right halves to detect these subtle changes in a non-perfusion scan. In specific examples, a mirror image of each image is taken and used as an input, along with the images (original images), to a machine learning model to identify the subtle, hard-to-detect differences corresponding to an ischemic condition (e.g., ischemic core, ischemic penumbra, ischemic stroke, etc.). This can have advantages over conventional attempts at solving this, which attempt to detect ischemic changes through primarily thresholding the set of images based on a particular pixel value threshold (e.g., a gray value), but variations throughout the brain (and throughout different patients and/or images) would either require a large amount of thresholds to be applied, often inaccurately, and/or the results would not be trustworthy.

In a tenth variation, additional or alternative to those described above, the system and/or method confers the benefit of automatically determining a potential ischemia (e.g., ischemic core) and/or a parameter associated with the ischemia (e.g., percentage and/or amount of brain irreversibly damaged, brain damage severity, brain damage location, brain function corresponding to damaged region, etc.) in a set of non-contrast scans and notifying a specialist prior to the identification of a potential brain ischemia by a radiologist during a parallel workflow. In conventional systems and methods, the contrast distinction of contrast images is required to detect (e.g., accurately detect) ischemic conditions.

In an eleventh variation, additional or alternative to those described above, the system and/or method confers the benefit of recommending a patient for a clinical trial based on an automated processing of a set of images (e.g., brain images) associated with the patient.

Additionally or alternatively, the system and method can confer any other benefit.

3. System

The system preferably interfaces with one or more points of care (e.g., $1^{st}$ point of care, $2^{nd}$ point of care, $3^{rd}$ point of care, etc.), which are each typically a healthcare facility. A $1^{st}$ point of care herein refers to the healthcare facility at which a patient presents, typically where the patient first presents (e.g., in an emergency setting). Conventionally, healthcare facilities include spoke facilities, which are often general (e.g., non-specialist, emergency, etc.) facilities, and hub (e.g., specialist) facilities, which can be equipped or better equipped (e.g., in comparison to spoke facilities) for certain procedures (e.g., mechanical thrombectomy), conditions (e.g., stroke), or patients (e.g., high risk). Patients typically present to a spoke facility at a $1^{st}$ point of care, but can alternatively present to a hub facility, such as when it is evident what condition their symptoms reflect, when they have a prior history of a serious condition, when the condition has progressed to a high severity, when a hub facility is closest, randomly, or for any other reason. A healthcare facility can include any or all of: a hospital, clinic, ambulances, doctor's office, imaging center, laboratory, primary stroke center (PSC), comprehensive stroke center (CSC), stroke ready center, interventional ready center, or any other suitable facility involved in patient care and/or diagnostic testing.

A patient can be presenting with symptoms of a condition, no symptoms (e.g., presenting for routine testing), or for any other suitable symptoms. In some variations, the patient is presenting with one or more stroke symptoms (e.g., vessel occlusion symptoms), such as, but not limited to: weakness, numbness, speech abnormalities, and facial drooping. Typically, these patients are then treated in accordance with a stroke protocol, which typically involves an imaging protocol at an imaging modality, such as, but not limited to: a non-contrast CT (NCCT) scan of the head, a CTA scan of the head and neck, a CT perfusion (CTP) scan of the head.

A healthcare worker herein refers to any individual or entity associated with a healthcare facility, such as, but not limited to: a physician, emergency room physician (e.g., orders appropriate lab and imaging tests in accordance with a stroke protocol), radiologist (e.g., on-duty radiologist, healthcare worker reviewing a completed imaging study, healthcare working authoring a final report, etc.), neuroradiologist, specialist (e.g., neurovascular specialist, vascular neurologist, neuro-interventional specialist, neuro-endovascular specialist, expert/specialist in a procedure such as mechanical thrombectomy, cardiac specialist, etc.), administrative assistant, healthcare facility employee (e.g., staff employee), emergency responder (e.g., emergency medical technician), or any other suitable individual.

The image data can include computed tomography (CT) data (e.g., radiographic CT, non-contrast CT, CT perfusion, etc.), preferably non-contrast CT data (e.g., axial data, axial series of slices, consecutive slices, etc.) but can additionally or alternatively any other suitable image data. The image data is preferably generated at an imaging modality (e.g., scanner at the $1^{st}$ point of care), such as a CT scanner, magnetic resonance imaging (MRI) scanner, ultrasound system, or any other scanner. Additionally or alternatively, image data can be generated from a camera, user device, accessed from a database or web-based platform, drawn, sketched, or otherwise obtained.

In some variations, the image data includes a set of non-perfusion CT images. While CT perfusion (CTP) images would likely make any brain tissue injury and/or death (e.g., ischemic penumbra, ischemic core, etc.) much more visible than in non-perfusion images, the time required to perform a non-perfusion scan is significantly less, which can provide more and better options treatment options for the patient, as well as decrease a total amount of irreversible tissue damage.

3.1 System—Router 110

The system 100 can include a router no (e.g., medical routing system), which functions to receive a data packet (e.g., dataset) including instances (e.g., images, scans, etc.) taken at an imaging modality (e.g., scanner) via a computing system (e.g., scanner, workstation, PACS server) associated with a $1^{st}$ point of care. The instances are preferably in the Digital Imaging and Communications in Medicine (DICOM) file format, as well as generated and transferred between computing system in accordance with a DICOM protocol, but can additionally or alternatively be in any suitable format. Additionally or alternatively, the instances can include any suitable medical data (e.g., diagnostic data, patient data, patient history, patient demographic information, etc.), such as, but not limited to, PACS data, Health-Level 7 (HL7) data, electronic health record (EHR) data, or any other suitable data, and to forward the data to a remote computing system.

The instances preferably include (e.g., are tagged with) and/or associated with a set of metadata, but can additionally or alternatively include multiple sets of metadata, no metadata, extracted (e.g., removed) metadata (e.g., for regulatory purposes, HIPAA compliance, etc.), altered (e.g., encrypted, decrypted, etc.) metadata, or any other suitable metadata, tags, identifiers, or other suitable information.

The router 110 can refer to or include a virtual entity (e.g., virtual machine, virtual server, etc.) and/or a physical entity (e.g., local server). The router can be local (e.g., at a $1^{st}$ healthcare facility, $2^{nd}$ healthcare facility, etc.) and associated with (e.g., connected to) any or all of: on-site server associated with any or all of the imaging modality, the healthcare facility's PACS architecture (e.g., server associated with physician workstations), or any other suitable local server or DICOM compatible device(s). Additionally or alternatively, the router can be remote (e.g., locate at a remote facility, remote server, cloud computing system, etc.), and associated with any or all of: a remote server associated with the PACS system, a modality, or another DICOM compatible device such as a DICOM router.

The router 110 preferably operates on (e.g., is integrated into) a system (e.g., computing system, workstation, server, PACS server, imaging modality, scanner, etc.) at a $1^{st}$ point of care but additionally or alternatively, at a $2^{nd}$ point of care, remote server (e.g., physical, virtual, etc.) associated with one or both of the $1^{st}$ point of care and the $2^{nd}$ point of care (e.g., PACS server, EHR server, HL7 server), a data storage system (e.g., patient records), or any other suitable system. In some variations, the system that the router operates on is physical (e.g., physical workstation, imaging modality, scanner, etc.) but can additionally or alternatively include virtual components (e.g., virtual server, virtual database, cloud computing system, etc.).

The router 110 is preferably configured to receive data (e.g., instances, images, study, series, etc.) from an imaging modality, preferably an imaging modality (e.g., CT scanner, MRI scanner, ultrasound machine, etc.) at a first point of care (e.g., spoke, hub, etc.) but can additionally or alternatively be at a second point of care (e.g., hub, spoke, etc.), multiple points of care, or any other healthcare facility. The router can be coupled in any suitable way (e.g., wired connection, wireless connection, etc.) to the imaging modality (e.g., directly connected, indirectly connected via a PACS server, etc.). Additionally or alternatively, the router 100 can be connected to the healthcare facility's PACS architecture, or other server or DICOM-compatible device of any point of care or healthcare facility.

In some variations, the router includes a virtual machine operating on a computing system (e.g., computer, workstation, user device, etc.), imaging modality (e.g., scanner), server (e.g., PACS server, server at $1^{st}$ healthcare facility, server at $2^{nd}$ healthcare facility, etc.), or other system. In a specific example, the router is part of a virtual machine server. In another specific example, the router is part of a local server.

3.2 System—Remote Computing System 120

The system 100 can include a remote computing system 120, which can function to receive and process data packets (e.g., dataset from router), determine a treatment option (e.g., select a $2^{nd}$ point of care, select a specialist, etc.), interface with a user device (e.g., mobile device), compress a data packet, extract and/or remove metadata from a data packet (e.g., to comply with a regulatory agency), or perform any other suitable function.

Preferably, part of the method 200 is performed at the remote computing system (e.g., cloud-based), but additionally or alternatively all of the method 200 can be performed at the remote computing system, the method 200 can be performed at a local computing system (e.g., at a healthcare facility), any other suitable computing system(s). In some variations, the remote computing system 120 provides an interface for technical support (e.g., for a client application) and/or analytics. In some variations, the remote computing system includes storage and is configured to store and/or access a lookup table, wherein the lookup table functions to determine a treatment option (e.g., $2^{nd}$ point of care), a contact associated with the $2^{nd}$ point of care, and/or any other suitable information.

In some variations, the remote computing system 120 connects multiple healthcare facilities (e.g., through a client application, through a messaging platform, etc.).

In some variations, the remote computing system 120 functions to receive one or more inputs and/or to monitor a set of client applications (e.g., executing on user devices, executing on workstations, etc.).

3.3 System—Application 130

Figure 5A:
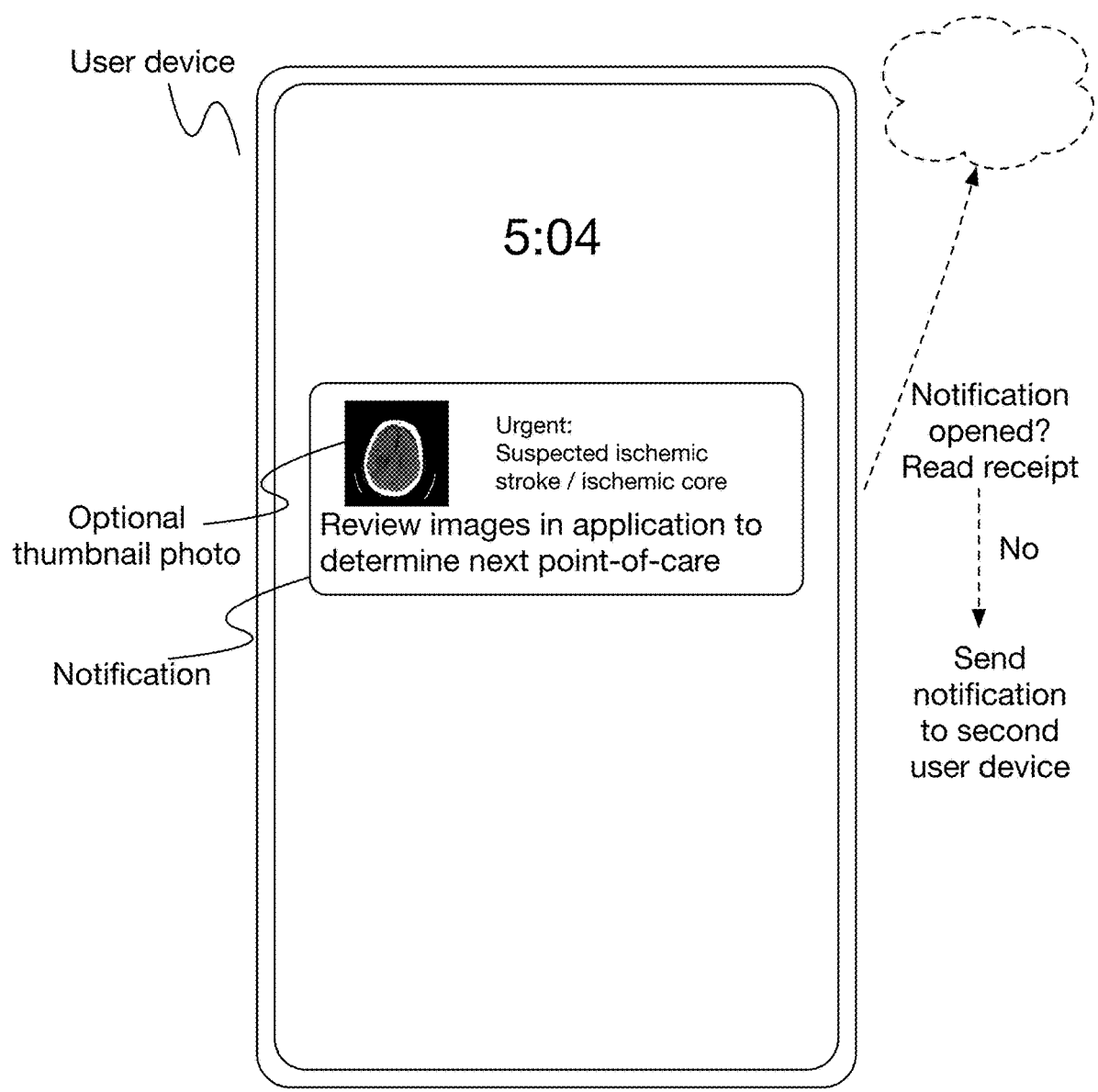
FIGS. 5A and 5B depict a variation of an application on a user device.
Figure 5B:
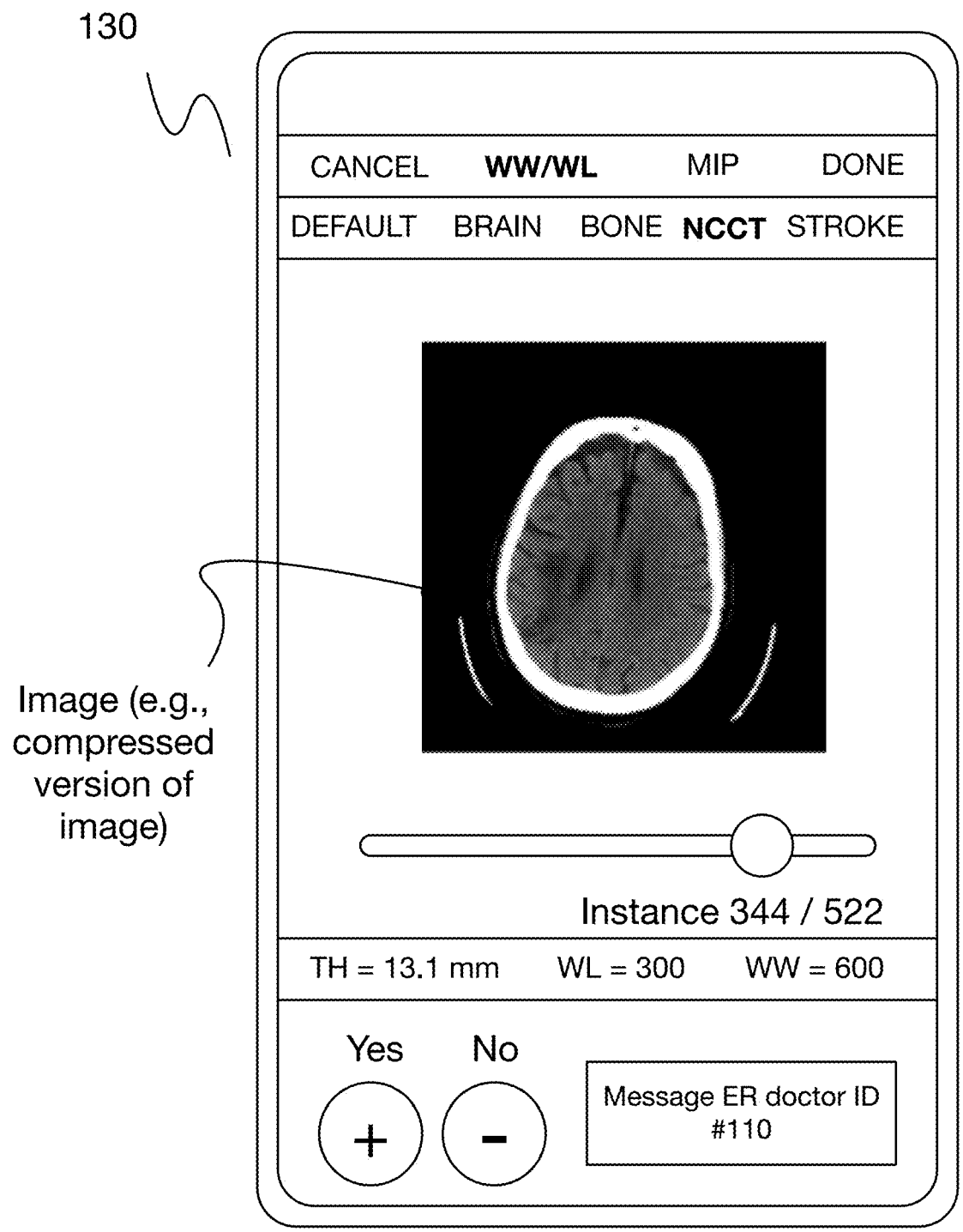

The system 100 can include one or more applications 130 (e.g., clients, client applications, client application executing on a device, etc.), such as the application shown in FIGS. 5A and 5B, which individually or collectively function to provide one or more outputs (e.g., from the remote computing system) to a contact. Additionally or alternatively, the applications can individually or collectively function to receive one or more inputs from a contact, provide one or more outputs to a healthcare facility (e.g., first point of care, second point of care, etc.), establish communication between healthcare facilities, or perform any other suitable function.

In some variations, one or more features of the application (e.g., appearance, information content, information displayed, user interface, graphical user interface, etc.) are determined based on any or all of: the type of device that the application is operating on (e.g., user device vs. healthcare facility device, mobile device vs. stationary device), where the device is located (e.g., $1^{st}$ point of care, $2^{nd}$ point of care, etc.), who is interacting with the application (e.g., user identifier, user security clearance, user permission, etc.), or any other characteristic. In some variations, for instance, an application executing on a healthcare facility will display a $1^{st}$ set of information (e.g., uncompressed images, metadata, etc.) while an application executing on a user device will display a $2^{nd}$ set of information (e.g., compressed images, no metadata, etc.). In some variations, the type of data to display is determined based on any or all of: an application identifier, mobile device identifier, workstation identifier, or any other suitable identifier.

The outputs of the application can include any or all of: an alert or notification (e.g., push notification, text message, call, email, etc.); an image set (e.g., compressed version of images taken at scanner, preview of images taken at scanner, images taken at scanner, etc.); a set of tools for interacting with the image set, such as any or all of panning, zooming, rotating, window leveling, scrolling, maximum intensity projection [MIP] (e.g., option to select the slab thickness of a MIP); changing the orientation of 3D scan (e.g., changing between axial, coronal, and sagittal views), showing multiple views of a set of images; a worklist (e.g., list of patients presenting for and/or requiring care, patients being taken care of by specialist, patients recommended to specialist, procedures to be performed by specialist, etc.); a messaging platform (e.g., HIPAA-compliant messaging platform, texting platform, video messaging, etc.); a telecommunication platform (e.g., video conferencing platform); a directory of contact information (e.g., $1^{st}$ point of care contact info, $2^{nd}$ point of care contact info, etc.); tracking of a workflow or activity (e.g., real-time or near real-time updates of patient status/workflow/etc.); analytics based on or related to the tracking (e.g., predictive analytics such as predicted time remaining in radiology workflow or predicted time until stroke reaches a certain severity; average time in a workflow, average time to transition to a second point of care, etc.); or any other suitable output.

The inputs can include any or all of the outputs described previously, touch inputs (e.g., received at a touch-sensitive surface), audio inputs, optical inputs, or any other suitable input. The set of inputs preferably includes an input indicating receipt of an output by a contact. This can include an active input from the contact (e.g., contact makes selection at application), a passive input (e.g., read receipt), or any other input.

In one variation, the system 100 includes a mobile device application 130 and a workstation application 130—both connected to the remote computing system—wherein a shared user identifier (e.g., specialist account, user account, etc.) can be used to connect the applications (e.g., retrieve a case, image set, etc.) and determine the information to be displayed at each application (e.g., variations of image datasets). In one example, the information to be displayed (e.g., compressed images, high-resolution images, etc.) can be determined based on: the system type (e.g., mobile device, workstation), the application type (e.g., mobile device application, workstation application,), the user account (e.g., permissions, etc.), any other suitable information, or otherwise determined.

The application can include any suitable algorithms or processes for analysis, and part or all of the method 200 can be performed by a processor associated with the application.

The application preferably includes both front-end (e.g., application executing on a user device, application executing on a workstation, etc.) and back-end components (e.g., software, processing at a remote computing system, etc.), but can additionally or alternatively include just front-end or back-end components, or any number of components implemented at any suitable system(s).

3.4 System—Additional Components

The system 100 and/or or any component of the system 100 can optionally include or be coupled to any suitable component for operation, such as, but not limited to: a processing module (e.g., processor, microprocessor, etc.), control module (e.g., controller, microcontroller), power module (e.g., power source, battery, rechargeable battery, mains power, inductive charger, etc.), sensor system (e.g., optical sensor, camera, microphone, motion sensor, location sensor, etc.), or any other suitable component.

3.5 System—Variations

In one variation, the system includes a router 110, which operates at a computing system at a $1^{st}$ point of care and receives image data from an imaging modality. The router transmits the image data to a remote computing system, wherein a series of algorithms (e.g., machine learning algorithms) are performed at the remote computing system, which determines a hypothesis for whether or not a suspected condition (e.g., ischemic core) is present based on the image data and/or any associated metadata. Based on the determination, a contact is determined from a lookup table (e.g., in storage at the remote computing system), wherein the contact is notified at a user device (e.g., personal device) and sent image data through a client application executing on the user device. One or more inputs from the contact at the application can be received at the remote computing system, which can be used to determine a next point of care for the patient.

Additionally or alternatively, any or all of the computing can be performed at a local computing system (e.g., at the $1^{st}$ point of care), a computing system associated with a user device, and/or any other suitable computing system.

4. Method

As shown in FIG. 2, a method 200 for computer-aided triage includes receiving a data packet associated with a patient and taken at a first point of care S205; checking for a suspected condition associated with the data packet S220; in an event that the suspected condition is detected, determining a recipient based on the suspected condition S230; and transmitting information to a device associated with the recipient S250. Additionally or alternatively, the method 200 can include any or all of: transmitting data to a remote computing system S208; preparing a data packet for analysis S210; determining a parameter associated with a data packet; determining a treatment option based on the parameter; preparing a data packet for transfer S240; receiving an input from the recipient; initiating treatment of the patient; transmitting information to a device associated with a second point of care; aggregating data; and/or any other suitable processes. Further additionally or alternatively, the method 200 can include any or all of the processes, embodiments, and examples described in any or all of: U.S. application Ser. No. 16/012,458, filed 19 Jun. 2018; and U.S. application Ser. No. 16/012,495, filed 19 Jun. 2018; U.S. application Ser. No. 16/688,721, filed 19 Nov. 2019; and U.S. application Ser. No. 16/913,754, filed 26 Jun. 2020; each of which is incorporated in its entirety by this reference, or any other suitable processes performed in any suitable order. The method 200 can be performed with a system 100 as described above and/or any other suitable system.

Figure 3:
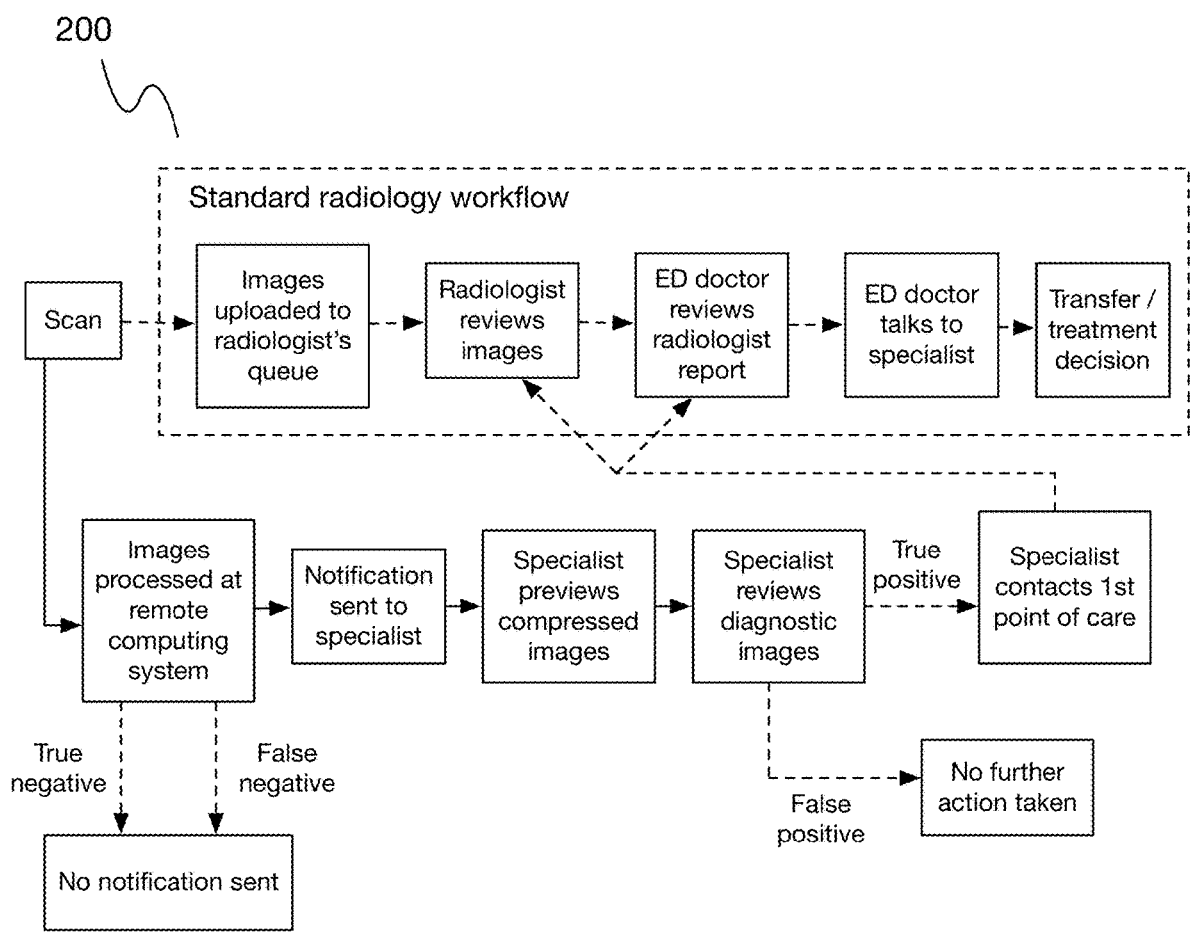
FIG. 3 depicts a variation of a method for computer-aided triage.

The method 200 can optionally be performed separate from but in parallel with (e.g., contemporaneously with, concurrently with, etc.) a standard radiology workflow (e.g., as shown in FIG. 3), but can additionally or alternatively be implemented within a standard workflow, be performed at a separate time with respect to a standard workflow, or be performed at any suitable time.

The method 200 can be partially or fully implemented with the system 100 or with any other suitable system.

The method 200 functions to improve communication across healthcare facility networks (e.g., stroke networks, spokes and hubs, etc.) and decrease the time required to transfer a patient having a suspected time-sensitive condition (e.g., brain condition, stroke, ischemic penumbra, ischemic core, hemorrhagic stroke, ischemic stroke, large vessel occlusion (LVO), cardiac event, trauma, etc.) from a first point of care (e.g., spoke, non-specialist facility, stroke center, ambulance, etc.) to a second point of care (e.g., hub, specialist facility, comprehensive stroke center, etc.), wherein the second point of care refers to a healthcare facility equipped to treat the patient. In some variations, the second point of care is the first point of care, wherein the patient is treated at the healthcare facility to which he or she initially presents.

The method 200 can optionally function as a parallel workflow tool, wherein the parallel workflow is performed contemporaneously with (e.g., concurrently, during, partially during) a standard radiology workflow (e.g., radiologist queue), but can additionally or alternatively be implemented within a standard workflow (e.g., to automate part of a standard workflow process, decrease the time required to perform a standard workflow process, etc.), be performed during a workflow other than a radiology workflow (e.g., during a routine examination workflow), or at any other suitable time.

The method 200 is preferably performed in response to a patient presenting at a first point of care. The first point of care can be an emergency setting (e.g., emergency room, ambulance, imaging center, etc.), equivalently referred to herein as an acute setting, or any suitable healthcare facility, such as those described previously. The patient is typically presenting with (or suspected to be presenting with) a time-sensitive condition, such as a neurovascular condition (e.g., stroke, brain tissue injury, brain tissue death, ischemic stroke, ischemia, ischemic core, ischemic penumbra, occlusion, large vessel occlusion (LVO), thrombus, aneurysm, etc.), cardiac event or condition (e.g., cardiovascular condition, heart attack, etc.), trauma (e.g., acute trauma, blood loss, etc.), or any other time-sensitive (e.g., life-threatening) condition. In other variations, the method is performed for a patient presenting to a routine healthcare setting (e.g., non-emergency setting, clinic, imaging center, etc.), such as for routine testing, screening, diagnostics, imaging, clinic review, laboratory testing (e.g., blood tests), or for any other reason.

Any or all of the method can be performed using any number of machine learning (e.g., deep learning) modules. Each module can utilize one or more of: supervised learning (e.g., using logistic regression, using back propagation neural networks, using random forests, decision trees, etc.), unsupervised learning (e.g., using an Apriori algorithm, using K-means clustering), semi-supervised learning, reinforcement learning (e.g., using a Q-learning algorithm, using temporal difference learning), and any other suitable learning style. Each module of the plurality can implement any one or more of: a regression algorithm (e.g., ordinary least squares, logistic regression, stepwise regression, multivariate adaptive regression splines, locally estimated scatterplot smoothing, etc.), an instance-based method (e.g., k-nearest neighbor, learning vector quantization, self-organizing map, etc.), a regularization method (e.g., ridge regression, least absolute shrinkage and selection operator, elastic net, etc.), a decision tree learning method (e.g., classification and regression tree, iterative dichotomiser 3, C4.5, chi-squared automatic interaction detection, decision stump, random forest, multivariate adaptive regression splines, gradient boosting machines, etc.), a Bayesian method (e.g., naïve Bayes, averaged one-dependence estimators, Bayesian belief network, etc.), a kernel method (e.g., a support vector machine, a radial basis function, a linear discriminate analysis, etc.), a clustering method (e.g., k-means clustering, expectation maximization, etc.), an associated rule learning algorithm (e.g., an Apriori algorithm, an Eclat algorithm, etc.), an artificial neural network model (e.g., a Perceptron method, a back-propagation method, a Hopfield network method, a self-organizing map method, a learning vector quantization method, etc.), a deep learning algorithm (e.g., a restricted Boltzmann machine, a deep belief network method, a convolution network method, a stacked autoencoder method, etc.), a dimensionality reduction method (e.g., principal component analysis, partial lest squares regression, Sammon mapping, multidimensional scaling, projection pursuit, etc.), an ensemble method (e.g., boosting, boostrapped aggregation, AdaBoost, stacked generalization, gradient boosting machine method, random forest method, etc.), V-nets, U-nets, and/or any suitable form of machine learning algorithm. Each module can additionally or alternatively be a: probabilistic module, heuristic module, deterministic module, or be any other suitable module leveraging any other suitable computation method, machine learning method, or combination thereof.

In preferred variations, a set of U-nets and/or V-nets are used in a segmentation process to identify and isolate brain matter corresponding to a suspected patient condition (e.g., ischemic core, ischemic penumbra, ischemic stroke, etc.).

Each module can be validated, verified, reinforced, calibrated, or otherwise updated based on newly received, up-to-date measurements; past measurements recorded during the operating session; historic measurements recorded during past operating sessions; or be updated based on any other suitable data. Each module can be run or updated: once; at a predetermined frequency; every time the method is performed; every time an unanticipated measurement value is received; or at any other suitable frequency. The set of modules can be run or updated concurrently with one or more other modules, serially, at varying frequencies, or at any other suitable time. Each module can be validated, verified, reinforced, calibrated, or otherwise updated based on newly received, up-to-date data; past data or be updated based on any other suitable data. Each module can be run or updated: in response to determination of an actual result differing from an expected result; or at any other suitable frequency.

4.1 Method—Receiving a Data Packet Associated with a Patient and Taken at a First Point of Care S205

The method 200 includes receiving data (e.g., data packet) associated with a patient and taken at a first point of care S205, which functions to collect data relevant to assessing a patient condition.

The data is preferably received at a router 110, wherein the router is in the form of a virtual machine operating on a computing system (e.g., computer, workstation, quality assurance (QA) workstation, reading workstation, PACS server, etc.) coupled to or part of an imaging modality (e.g., CT scanner, MRI scanner, etc.), or any other suitable router. Additionally or alternatively, data can be received at a remote computing system (e.g., from an imaging modality, from a database, a server such as a PACS server, an internet search, social media, etc.), or at any other suitable computing system (e.g., server) or storage site (e.g., database). In some variations, for instance, a subset of the data (e.g., image data) is received at the router while another subset of the data (e.g., patient information, patient history, etc.) is received at a remote computing system. In a specific example, the data subset received at the router is eventually transmitted to the remote computing system for analysis.

S205 is preferably performed in response to (e.g., after, in real time with, substantially in real time with, with a predetermined delay, with a delay of less than 10 seconds, with a delay of less than 1 minute, at the prompting of a medical professional, etc.) the data (e.g., each of a set of instances) being generated at the imaging modality. Additionally or alternatively, S205 can be performed in response to a set of multiple instances being generated by the imaging modality (e.g., after a partial series has been generated, after a full series has been generated, after a study has been generated, etc.), in response to a metadata tag being generated (e.g., for an instance, for a series, for a study, etc.), in response to a trigger (e.g., request for images), throughout the method (e.g., as a patient's medical records are accessed, as information is entered a server, as information is retrieved from a server, etc.), or at any other suitable time.

S205 can be performed a single time or multiple times (e.g., sequentially, at different times in the method, once patient condition has progressed, etc.). In one variation, each instance is received (e.g., at a router, at a remote computing system, etc.) individually as it is generated. In a second variation, a set of multiple instances (e.g., multiple images, full series, etc.) are received together (e.g., after a scan has completed, after a particular anatomical component has been imaged, etc.).

The router (e.g., virtual machine, virtual server, application running on the image sampling system or a computing system connected to the image sampling system, etc.) can be continuously 'listening' (e.g., operating in a scanning mode, receiving mode, coupled to or include a radio operating in a suitable mode, etc.) for information from the imaging modality, can receive information in response to prompting of a healthcare facility worker, in response to a particular scan type being initiated (e.g., in response to a head CTA scan being initiated), or in response to any other suitable trigger.

Image data is preferably received at the router (e.g., directly, indirectly, etc.) from the imaging modality (e.g., scanner) at which the data was generated. Additionally or alternatively, image data or any other data can be received from any computing system associated with the healthcare facility's PACS server, any DICOM-compatible devices such as a DICOM router, or any other suitable computing system. The image data is preferably in the DICOM format but can additionally or alternatively include any other data format.

In addition to or alternative to image data, the data can include blood data, electronic medical record (EMR) data, unstructured EMR data, health level 7 (HL7) data, HL7 messages, clinical notes, or any other suitable data related to a patient's medical state, condition, or medical history.

The data preferably includes image data including a set of one or more instances (e.g., images), which can be unorganized, organized (e.g., into a series, into a study, a sequential set of instances based on instance creation time, acquisition time, image position, instance number, unique identification (UID), other acquisition parameters or metadata tags, anatomical feature or location within body, etc.), complete, incomplete, randomly arranged, or otherwise arranged.

The image data is preferably received from (imaged at) a scanner. The scanner can include any or all of: a computed tomography (CT) scanner, a magnetic resonance imaging (MRI) scanner, an ultrasound system, an X-Ray scanner, and/or any other suitable imaging device (e.g., camera). The set of images can include any or all of: CT images (e.g., non-contrast CT [NCCT] images, contrast CT images, CT angiography images, etc.); MRI images; X-ray images; ultrasound images; and/or any other suitable images produced by any or all of these imaging devices or others.

In preferred variations for detecting ischemic core, the set of images preferably includes NCCT images of the patient's head.

Each instance preferably includes (e.g., is tagged with) a set of metadata associated with the image dataset, such as, but not limited to: one or more patient identifiers (e.g., name, identification number, UID, etc.), patient demographic information (e.g., age, race, sex, etc.), reason for presentation (e.g. presenting symptoms, medical severity score, etc.), patient history (e.g., prior scans, prior diagnosis, prior medical encounters, etc.), medical record (e.g. history of present illness, past medical history, allergies, medications, family history, social history, etc.), scan information, scan time, scan type (e.g., anatomical region being scanned, scanning modality, scanner identifier, etc.), number of images in scan, parameters related to scan acquisition (e.g., timestamps, dosage, gurney position, scanning protocol, contrast bolus protocol, etc.), image characteristics (e.g., slice thickness, instance number and positions, pixel spacing, total number of slices, etc.), or any other suitable information.

In some variations, any or all of the data (e.g., image data) is tagged with metadata associated with the standard DICOM protocol.

In some variations, one or more tags is generated and/or applied to the data after the data is generated at an imaging modality. In some examples, the tag is an identifier associated with the $1^{st}$ point of care (e.g., $1^{st}$ point of care location, imaging modality identifier, etc.), which can be retrieved by a $2^{nd}$ point of care in order to locate the patient (e.g., to enable a quick transfer of the patient, to inform a specialist of who to contact or where to reach the patient, etc.).

Additionally or alternatively, image data can be received without associated metadata (e.g., metadata identified later in the method, dataset privately tagged later with metadata later in the method, etc.).

In a first set of variations for detecting an ischemic condition (e.g., ischemic core, ischemic penumbra, ischemic stroke, etc.), metadata of images are checked for metadata inclusion criteria, including/indicating any or all of: a CT scan of the head, a non-contrast CT scan of the head, an axial series, a slice thickness within a supported range, the absence of missing slices, aligned instance numbers and positions, patient age above a minimum threshold (e.g., between 0 and 10, between 10 and 20, between 20 and 30, above 30, etc.), consistent pixel spacing, a total number of slices within a predetermined range (e.g., between 18 and 25), and/or any other suitable metadata inclusion criteria.

Data can be received (e.g., at the router) through a wired connection (e.g., local area network (LAN) connection), wireless connection, or through any combination of connections and information pathways.

In a first variation, e.g., for a patient presenting with symptoms of an ischemic stroke, ischemic core, ischemic penumbra, etc.), S205 includes receiving a non-perfusion CT (NCCT) scan of a patient's head. In a preferred specific example of this variation, the non-perfusion CT scan includes an axial series of image instances (equivalently referred to herein as slices), each of the slices corresponding to an axial thickness between 2.5 and 5 millimeters, wherein the axial series includes no missing slices and wherein the slices are properly ordered (e.g., instance numbers and positions aligned).

4.2 Method—Transmitting Data to a Remote Computing System S208

The method can include transmitting data to a remote computing system (e.g., remote server, PACS server, etc.) S208, which functions to enable remote processing of the data, robust process, or fast processing (e.g., faster than analysis done in clinical workflow, faster than done in a standard radiology workflow, processing less than 20 minutes, less than 10 minutes, less than 7 minutes, etc.) of the dataset.

The data (e.g., image data, image data and metadata, etc.) is preferably transmitted to a remote computing system from a router (e.g., virtual machine operating on a scanner) connected to a computing system (e.g., scanner, workstation, PACS server, etc.) associated with a healthcare facility, further preferably where the patient first presents (e.g., $1^{st}$ point of care), but can additionally or alternatively be transmitted from any healthcare facility, computing system, or storage site (e.g., database).

Each instance (e.g., image) of the dataset (e.g., image dataset) is preferably sent individually as it is generated at an imaging modality and/or received at a router, but additionally or alternatively, multiple instances can be sent together after a predetermined set (e.g., series, study, etc.) has been generated, after a predetermined interval of time has passed (e.g., instances sent every 10 seconds), upon the prompting of a medical professional, or at any other suitable time. Further additionally or alternatively, the order in which instances are sent to a remote computing system can depend one or more properties of those instances (e.g., metadata). S208 can be performed a single time or multiple times (e.g., after each instance is generated).

S208 can include transmitting all of the dataset (e.g., image dataset and metadata), a portion of the dataset (e.g., only image dataset, subset of image dataset and metadata, etc.), or any other information or additional information (e.g., supplementary information such as supplementary user information).

The data is preferably transmitted through a secure channel, further preferably through a channel providing error correction (e.g., over TCP/IP stack of $1^{st}$ point of care), but can alternatively be sent through any suitable channel.

S208 can include any number of suitable sub-steps performed prior to or during the transmitting of data to the remote computing system. These sub-steps can include any or all of: encrypting any or all of the dataset (e.g., patient information) prior to transmitting to the remote computing system, removing information (e.g., sensitive information), supplementing the dataset with additional information (e.g., supplementary patient information, supplemental series of a study, etc.), compressing any or all of the dataset, or performing any other suitable process.

4.3 Method—Preparing a Data Packet for Analysis S210

The method 200 preferably includes preparing a data packet S210 for analysis (e.g., pre-processing), which can function to pre-process any or all of the data packet, eliminate an irrelevant (e.g., incorrectly labeled, irrelevant anatomical region, etc.) or unsuitable data packet from further analysis, produce one or more inputs for future processes in the method (e.g., an overlaid registered image), or perform any other suitable function.

S210 can optionally include resizing one or more of the set of instances, which can function to reduce an amount of data being processed in future processes. Additionally, resizing can function to shorten the time of transfer of data between points of the system (e.g., from a virtual machine to a remote computing system, from a remote computing system to a mobile device and/or workstation, etc.), and therefore subsequently reduce a total time required to process the data. Resizing the set of instances can be performed in accordance with (e.g., as part of, contemporaneously with, based on the results of, etc.) one or more registration processes, such as—but not limited to—any or all of the registration processes described below (e.g., a first set of registration processes, a second set of registration processes, etc.). Additionally or alternatively, the set of instances can be resized to particular image size (e.g., predetermined image size, dynamically determined image size, through downsampling, through lossless compression, through lossy compression, etc.). In one variation, for instance, S210 includes resizing each of the set of instances from 512×512 to 256×256 or from 512×512 to 96×96.

Additionally or alternatively, S210 can include cropping one or more of the set of images (e.g., according to a predetermined crop size, to emphasize a particularly relevant region, to remove an unwanted region, to increase a uniformity of the region shown in a set of images, etc.), straightening out one or more of the set of images (e.g., rotating a portion of the image, translating a portion of the image, by registering each of a set of images with its mirror image, etc.), or otherwise pre-processing the set of images.

S210 can optionally include one or more registration processes (e.g., image registration processes), which function to align, scale, calibrate, or otherwise adjust the set of images. Alternatively, the images can proceed to future processes in absence of any registration processes. The registration process(es) can be performed through registering any or all of the set of images (e.g., soft matter regions extracted from set of images) to a reference set of images (e.g., reference series); additionally or alternatively, any or all of the registration process(es) can be performed in absence of comparing the present set of instances with a reference set of instances (e.g., by comparing a first region of one instance with a second region of the same instance, by comparing a right brain hemisphere of the instance with a left brain hemisphere of the same instance, by comparing one instance of the set of images with another instance of the set of images, by comparing an instance with a mirror image of itself, etc.).

The registration can optionally be performed in response to a data packet being filtered through a set of exclusion criteria. Additionally or alternatively, registration can be performed prior to or in absence of filtering, multiple times throughout the method, prior to filtering through a set of exclusion criteria, or at any other suitable time.

S210 can optionally include a first type of registration process, equivalently referred to herein as reference registration, wherein the set of images is registered against a reference set of images, which functions to align and/or scale the set of images. Additionally, this first registration process can function to identify a left and right hemisphere of the brain. The first registration process can be performed in response to receiving the set of images (e.g., prior to checking for a particular brain condition, prior to a second set of registration processes, etc.), after a set of exclusion criteria have been checked or in response to any other process, and/or at any other suitable time. Alternatively, the method can be performed in absence of a first set of registration processes.

The reference registration can be any or all of: intensity-based, feature-based, or otherwise configured, and can include any or all of: point-mapping, feature-mapping, or any other suitable process. The reference set of instances is preferably determined from a training set but can alternatively be determined from any suitable dataset, computer-generated, or otherwise determined. The reference series can be selected for any or all of orientation, size, three-dimensional positioning, clarity, contrast, or any other feature. In one variation, a references series is selected from a training set, wherein the reference series is selected based on a feature parameter (e.g., largest feature size such as largest skull dimension, smallest feature size, etc.) and/or a degree of alignment (e.g., maximal alignment, alignment above a predetermined threshold, etc.). Additionally or alternatively, any other criteria can be used to determine the reference series, the reference series can be randomly selected, formed from aggregating multiple sets of instances (e.g., multiple patient series), or determined in any other suitable way. In some variations, the registration is performed with one or more particular software packages (e.g., SimpleElastix). In a specific example, the registration is performed through affine registration (e.g., in SimpleElastix) with a set of predetermined (e.g., default) parameters and iterations (e.g., 4096 iterations, between 3000 and 5000 iterations, above 1000 iterations, above 100 iterations, etc.) in each registration step.

S210 preferably includes a second type of registration processes, equivalently referred to herein as intra-image registration, which functions to enable a comparison between multiple parts of a single image. This can enable, for instance, a comparison between a right brain hemisphere (e.g., in size, position, angle, etc.) and a left brain hemisphere from the same image instance. This can be used (e.g., at a later process in the method) to compare (e.g., map to) an area of injured tissue (e.g., ischemic penumbra, ischemic core, etc.) in a first brain region with a corresponding area in a second brain region (e.g., a mirror image region, an opposing region, etc.). In a first variation, for instance, for a set of one or more images indicating a potential ischemia in a left hemisphere, the area of injured tissue in the left hemisphere can be compared with a corresponding tissue region (e.g., horizontally opposing in an aligned brain image) in a right hemisphere (e.g., to determine if there is injured tissue, to confirm that there is injured tissue, to quantify or otherwise assess an amount of injured tissue, etc.). In a second variation, for instance, for a set of one or more images indicating a potential ischemia in a right hemisphere, the area of injured tissue in the right hemisphere can be compared with a corresponding tissue region (e.g., non-injured region) in the left hemisphere.

Figure 4:
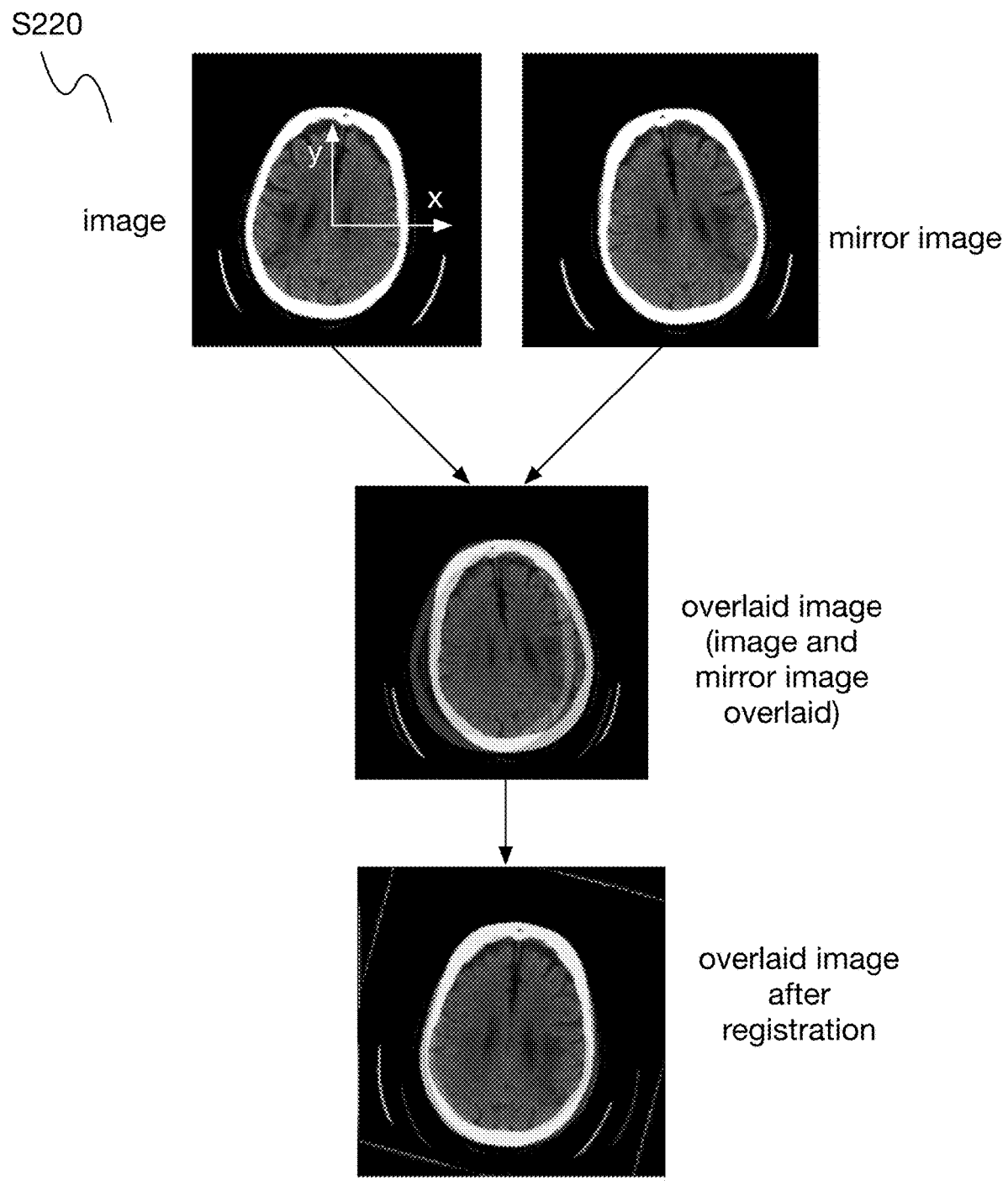
FIG. 4 depicts a variation of a portion of a method for computer-aided triage.

In preferred variations (e.g., as shown in FIG. 4), a registration process includes producing a second input for analysis, which can include any or all of: a mirror image of the each of the set of images (e.g., after the set of images have been registered with a first set of registration processes, the original set of images, etc.), an overlaid image including the image superimposed with (and optionally aligned with) its mirror image, a registered mirror image (e.g., taken as a mirrored version of the registered original image). The mirror image is preferably received concurrently (e.g., at the same time, at an overlapping time, immediately after, immediately before, etc.) with its corresponding non-mirror image (e.g., original image, registered original image, etc.) to on or more deep learning models, but can additionally or alternatively be received at different times (e.g., after). Having mirror images for comparison can ultimately function to enable subtle visual differences (e.g., a color difference below a predetermined threshold, a sulcal dimension difference [such as a difference in spacing between adjacent sulci] below a predetermined threshold, a "texture" difference below a predetermined threshold, etc.) between regions of the image (e.g., between corresponding regions in the left and right hemispheres) to be identified (e.g., with non-contrast scans). In these variations, for instance, a machine learning model can be trained and/or used to better detect subtle changes in brain matter (e.g., from non-contrast images) corresponding to an ischemic condition by receiving mirror images in addition to the set of images, which effectively enables ratios in contrast between corresponding left and right voxels to be utilized to determine ischemic regions. In specific examples, the mirror images are overlaid and aligned with the corresponding original images, wherein the original set of images and overlaid images are received as an input to the machine learning model(s).

Additionally or alternatively, and other suitable input(s) can be received

A mirror image of each image is preferably formed by taking a mirror image about a central axis (e.g., y-axis as shown in FIG. 4) of the image (e.g., prior to a first set of registrations steps, in absence of a first set of registration steps, after the set of images has been straightened out, in absence of the set of images being straightened out, etc.). Additionally or alternatively, a mirror image can be taken about an anatomical line (e.g., cerebral fissure) or any other suitable axis of the set of images. In some variations, a mirror image is produced based on an unregistered original image. In additional or alterative variations, a first mirror image is produced, which is used to register the original image, and then the mirror image is updated to be registered based on the registered original image (e.g., formed from the mirror image of the registered image). In specific examples, the registered mirror image is then overlaid with the registered original image. Additionally or alternatively, the original image and its mirror image can be registered together, not registered, not overlaid, and/or otherwise produced and/or modified.

Each image is preferably then superimposed with its mirror image, forming a superimposed image (equivalently referred to herein as the overlaid image). The superimposed image can then be registered to align the image with its mirror image in the superimposed image, forming a registered superimposed image (equivalently referred to herein as the registered overlaid image). This functions to align the left and right hemispheres, enable a mapping of a region in a first brain hemisphere to a corresponding region in the opposing hemisphere, straighten the overall scan, resize one or more regions of the scan (e.g., to correct for a nonzero z-angle of the patient in the scanner), and/or perform any other function. Alternatively, the image and its mirror image can remain separate (e.g., and be processed independently).

Additional or alternative to variations in which a mirror image is produced for each image, an intra-image registration process can include separating (e.g., dividing) each of the set of images (e.g., after a first set of image registration processes, in absence of a first set of image registration processes, etc.) into multiple parts, such as the left and right hemispheres (e.g., separating each image along a cerebral fissure). The hemispheres can be identified through any or all of: a first set of registration steps, a segmentation process, a windowing process (e.g., based on Hounsfield unit values), a geometrical division of each image (e.g., division along a centerline), or any other suitable process. The multiple parts of each image can then be processed in any suitable way (e.g., separately, together, etc.) for any remainder processes of the method. In a specific example, for instance, each of a set of brain images is divided into left and right hemispheres (e.g., separated along the longitudinal fissure, separated along a y-axis, separated along a y-axis after the image has been straightened out, etc.), wherein the set of left hemispheres and the set of right hemispheres are processed separately and the results compared.

S210 can optionally include windowing (equivalently referred to herein as clipping) the image data, which can function to increase the image contrast of a predetermined (e.g., desired) range (window) of pixel/voxel values (e.g., Hounsfield units), eliminate irrelevant information (e.g., information not corresponding to regions of interest/potential user conditions) from further processing, and/or perform any other suitable function. The threshold values (e.g., HU values) determining the window range can optionally be determined based on any or all of: the type of scan (e.g., contrast, non-contrast, CT, NCCT, MRI, etc.), the body region scanned (e.g., head), suspected condition (e.g., ischemic core, ischemic penumbra, ischemic stroke, etc.), patient demographics and/or metadata (e.g., age, gender, etc.), and/or any other suitable information. Additionally or alternatively, the threshold values can be constant for all images.

In some variations (e.g., for detecting brain conditions), the range of HU values that are retained for processing ranges from a Hounsfield unit just below that corresponding to soft matter to a Hounsfield unit just above that corresponding to bone. Additionally or alternatively, a window can be shifted with respect to this (e.g., anything below bone), narrowed with respect to this (e.g., only encompassing brain tissue), broadened with respect to this, or otherwise selected.

In specific examples, the information retained has HU values between 1000 and 2000.

Windowing the data can be performed after one or more registration processes, prior to one or more registration processes, during one or more registration processes, at another time, or at any combination of times. The window preferably ranges from a Hounsfield unit just below that corresponding to soft matter to a Hounsfield unit just above that corresponding to bone. Additionally or alternatively, a window can be shifted with respect to this (e.g., anything below bone), narrowed with respect to this (e.g., only encompassing brain tissue), broadened with respect to this, or otherwise selected.

S210 can further include an effective and/or actual removal (e.g., assignment of a pixel value of zero, actual removal through cropping, etc.) of one or more regions of the image, which can be performed after and/or based on a windowing process (e.g., as described above), but can additionally or alternatively be performed prior to a windowing process, in absence of a windowing process, in a later process (e.g., after a segmentation process), or otherwise performed. In one variation, a set of "white" regions (e.g., regions having a pixel/voxel value of 255, regions having a pixel/voxel value above a predetermined threshold, etc.) are assigned a pixel/voxel value of zero, which—in combination with a windowing process as described above—can function to result in the extraction of only soft matter (e.g., brain matter, blood, cerebral fluid, etc.); this can equivalently be referred to herein as skull stripping. Additionally or alternatively, any other regions can be effectively and/or actually removed in any suitable way (e.g., through photomasks, dilation, erosion, etc.).

S210 can also optionally include the normalization of any or all of the image data, which can function to enable the comparison of multiple images with each other, the comparison of one series with a different series (e.g., the series of a previously-taken brain scan, the series of one patient with a reference series, the series of a first patient that that of a second patient, etc.), or perform any other suitable function, such as faster training convergence of deep learning models in processing. In one variation, the set of voxels in the image data are normalized such that the voxels have a predetermined mean Hounsfield unit value (e.g., 24.5 HU, less than 24.5 HU, greater than 24.5 HU, etc.) and a predetermined standard deviation Hounsfield unit value (e.g., 39.5 HU, less than 39.5 HU, greater than 39.5 HU, etc.). In specific examples, the image data is normalized by dividing by a fixed number. Additionally or alternatively, the image data can be normalized in any other suitable way with respect to any suitable parameter and/or the method can be performed in absence of a normalization process.

S210 can optionally include organizing the set of images (e.g., instances, slices, scans, etc.), preferably into a series, but additionally or alternatively into a study, or any other suitable grouping of images. The organization is preferably performed in response to generating a set of images (e.g., at an imaging modality), but can additionally or alternatively be performed in response to receiving a set of instances at a location (e.g., router, remote computing system, server such as a PACS server, etc.), at the request of an individual (e.g., healthcare worker), in response to a trigger, in response to any other pre-processing step, or at any other suitable time.

In some variations, the method includes excluding a data packet (e.g., set of instances) from further processing if one or more of a set of metadata are not satisfied, such as, but not limited to, the metadata listed above.

In a specific example, a bone mask is determined and defined as a set of voxels having an HU value above a predetermined threshold (e.g., 750 HU, 700 HU, 800 HU, between 600 HU and 900 HU, etc.). The bone mask is then dilated with a series of kernels of increasing size until it completely encloses a set of voxels of low HU values (e.g., less than the predetermined threshold), thereby defining a soft matter mask. The soft matter mask is dilated to compensate for the dilation of the bone mask. If the process of defining the soft matter mask fails, this can indicate that the skull has undergone a craniotomy, which in some cases can be used in determining a diagnosis, informing a contact or second point of care, or in any other point in the method. Once the soft matter mask is dilated, the mask can then be applied to the set of instances (e.g., organized set of instances, series, etc.), and the HU value of voxels outside of the mask is set to zero.

In a first set of variations, S210 includes producing a mirror image of each of the set of images and overlaying and/or registering each of the set of images with its mirror image. Additionally or alternatively, S210 can include resizing each of a set of NCCT images to a predetermined uniform size (e.g., 256×256); windowing the NCCT images (e.g., to remove bone matter); and/or any other suitable processes.

4.4 Method—Checking for a Suspected Condition Associated with the Data Packet S220

Figure 13:
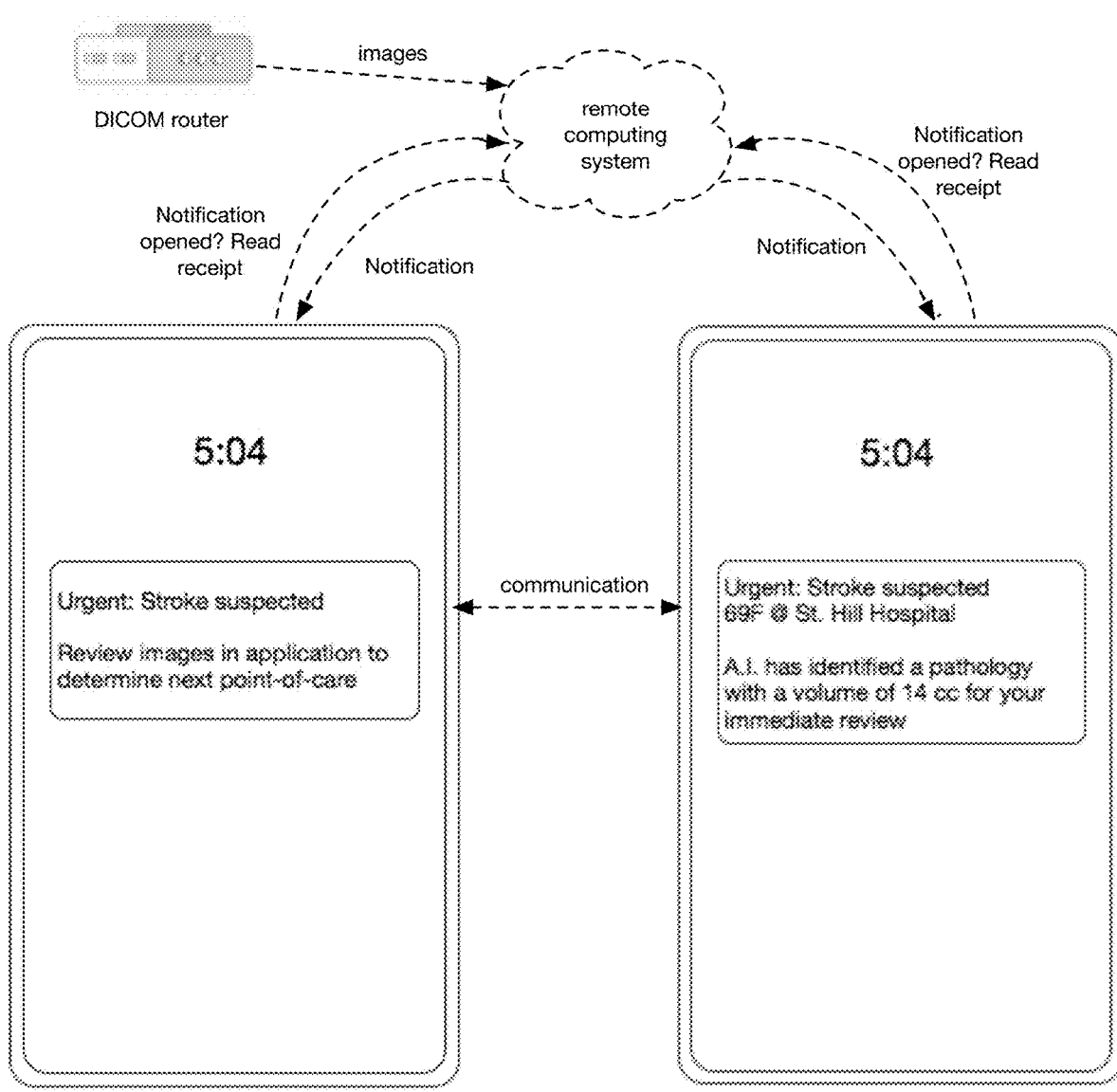
FIG. 13 depicts variations of a client application executing on first and second user devices.

The method 200 includes checking for a suspected condition and optionally one or more parameters of the suspected condition (e.g., as shown in FIG. 13) associated with the data packet S220, which functions to determine a region of image data proposed to be affected with a patient condition (e.g., brain ischemia) and inform the remaining processes of the method. Additionally or alternatively, S220 can function to reduce the time to transfer a patient to a second point of care, halt progression of the condition, or perform any other suitable function. S220 is preferably fully performed at a remote computing system (e.g., remote server, cloud-based server, etc.), further preferably a remote computing system having a graphics processing unit (GPU), but can additionally or alternatively be partially performed at any suitable remote computing system, be partially or fully performed at a local computing system (e.g., workstation), server (e.g., PACS server), at a processor of a user device, or at any other system. S220 is preferably partially or fully performed using software including one or more algorithms, further preferably one or more multi-step algorithms containing steps that are either trained (e.g., trained through machine learning, trained through deep learning, continuously trained, etc.) or non-trained (e.g., rule-based image processing algorithms or heuristics). Additionally or alternatively, any software can be implemented.

S220 preferably includes identifying (e.g., locating, isolating, measuring, quantifying, etc.) and optionally segmenting an affected brain region (e.g., injured tissue, ischemic tissue, ischemic core tissue, ischemic penumbra tissue, etc.) within one or more of the set of images, thereby indicating a brain condition (e.g., ischemia, ischemic stroke, etc.) or at least a potential brain condition (e.g., ischemia, ischemic core, ischemic stroke). This can be performed through any number of computer vision techniques, such as object recognition, object identification, object detection, or any other form of image analysis.

In cases of brain ischemia (e.g., ischemic core), the affected brain region can include and/or be characterized by any or all of: hypodensity, which can be depicted as a dark region in a brain scan (e.g., region having a pixel value [e.g., HU value] above a predetermined threshold, region having a pixel value exceeding a neighboring pixel value by a predetermined threshold, etc.); abnormal texture, which can be depicted as a loss of delineation in a region of the brain scan (e.g., region having an overall contrast [e.g., range of HU values] below a predetermined threshold, region having a spacing between detected features above a predetermined threshold, region having an expected feature [e.g., gyrus] missing, etc.); sulcal effacement, which can be depicted as a decreased fluid volume of one or more sulci (e.g., region having a distance between adjacent gyri below a predetermined threshold); or any other suitable feature.

As such, identifying an affected brain region (e.g., hypodense brain region) can include identifying (e.g., indirectly with a machine learning model, with a classically programmed model, etc.) image features associated with an ischemic condition based on a trained machine learning model. These features can include a pixel value and/or Hounsfield unit value outside of a "normal" range (e.g., above a predetermined threshold value, below a predetermined threshold value, outside a range of predetermined values, etc.). This can include, for instance, any or all of: identifying an image region having a pixel value above a predetermined threshold, identifying a region having a Hounsfield unit value above a predetermined threshold, identifying a region having a pixel value below a predetermined threshold, identifying a region having a Hounsfield unit value below a predetermined threshold, identifying a region which differs in pixel value from adjacent regions by a value above a predetermined threshold, identifying a region which differs in Hounsfield unit value from adjacent regions by a value above a predetermined threshold, or any other suitable region having defined by any suitable features. Additionally or alternatively, identifying an affected brain region can include identifying a region (e.g., of a uniform size, of a size above a predetermined threshold, etc.) having a delineation parameter below a predetermined threshold (e.g., by detecting a change in delineation with respect to an adjacent region above a predetermined threshold, by detecting a set of lines in the brain scan having a length below a predetermined threshold, etc.). Further additionally or alternatively, identifying an affected brain region can include identifying a region in which a set of sulci have terminated (e.g., uniformly terminated, suddenly terminated, gradually terminated, etc.) and/or experienced an abnormal spacing (e.g., through detecting a spacing between adjacent sulci below a predetermined threshold, through detecting a spacing between adjacent gyri below a predetermined threshold, through detecting a spacing between adjacent sulci above a predetermined threshold, through detecting a spacing between adjacent gyri above a predetermined threshold, etc.). Additionally or alternatively, identifying an affected brain region can include any other suitable processing of the set of images.

The image region can optionally be compared with one or more thresholds, the one or more thresholds can be any or all of: predetermined (e.g., constant, based on one or more anatomical values, based on one or more physiological values, based on an algorithm, based on an average value from a dataset, based on a maximum value from a dataset, based on a minimum value from a dataset, etc.), dynamically determined (e.g., specific to the user, based on a value in a corresponding region in the opposing hemisphere, based on a value found in the image dataset, etc.), any combination of predetermined and dynamically determined, or otherwise determined (e.g., without a set of thresholds).

Determining that a proposed brain region is potentially affected (e.g., and suitable for future processing) can require any or all of: the satisfaction of one of the above criteria (e.g., exceeding a threshold), the satisfaction of a predetermined number (e.g., 2 or more, 3 or more, all, etc.) of the above criteria, the presence of any other suitable criteria, or be otherwise determined.

Identifying an affected brain region (e.g., region of tissue death) preferably includes image segmentation (e.g., prior to comparing an affected region with a threshold), wherein the segmentation can include any or all of: thresholding, clustering methods, dual clustering methods, compression-based methods, histogram-based methods, region-growing methods, partial differential equation-based methods, variational methods, graph partitioning methods, watershed transformations, model based segmentation, multi-scale segmentation, semi-automatic segmentation, trainable segmentation, or any suitable form of segmentation. The method can additionally or alternatively include any number of segmentation post-processing steps, such as thresholding, connectivity analyses, or any other processing. The segmentation is preferably performed with a deep learning module including a convolutional neural network (CNN), further preferably any or all of: a U-Net, V-net, and/or any suitable feed-forward deep CNN (e.g., using three-dimensional convolutions, two-dimensional convolutions, etc.), but can additionally or alternatively be performed using any suitable models, algorithms, and/or or processes.

In some variations, for instance, S220 includes a segmentation process in the event of a suspected ischemia, wherein the segmentation process segments regions associated with early ischemic changes through a deep CNN, wherein the deep CNN was trained based on hand annotated training data. The segmentation process is preferably performed on a set of one or more images (e.g., slices, resized slices, etc.) wherein mirror images (e.g., overlaid registered images) are received at the deep CNN as an input, but can additionally or alternatively be performed on the overlaid image (e.g., registered overlaid image), and/or any other suitable image (s). In a first specific example, the segmentation process is performed on the set of image slices, wherein the segmentation process produces a segmented region corresponding to a suspected ischemic region based on analysis of the set of images and an overlaid set of images with the set of images and its mirror images (e.g., based on a ratio of voxels in the segmented region relative a mirror image exceeding a threshold).

The segmentation process can optionally include assigning one or more scores, such as a probability score (e.g., between 0 and 1) to each base unit (e.g., pixel, voxel, etc.) of the input, which indicates a likelihood that the base unit represents a part of the brain condition (e.g., ischemic core) or set of brain conditions being tested for. A segmentation region (e.g., initial segmentation region, final segmentation region, etc.) is then formed from the base units having a probability score above a predetermined threshold.

In one variation, the segmentation of a set of NCCT scan slices functions to segment regions which are consistent with an ischemic conditions. In a specific example, a 3D array is formed from the set of scan slices, the 3D array containing a set of probability values between 0 and 1 for each of the set of voxels in a 3D representation of the scan slices, the probability values corresponding to a likelihood that each voxel corresponds to an ischemic feature (e.g., as described above), such as based on comparison with a mirror image region. A set of voxels (e.g., contiguous voxels, connected voxels, bordering voxels, etc.), preferably adjacent (e.g., contiguous) voxels (but alternatively non-adjacent or partially adjacent voxels), having a ratio above a predetermined threshold in comparison with their mirror image counterparts represents a region suspected of having an ischemic condition. The probabilistic output of the network can then be converted into a binary mask defined as all voxels having a probability greater than this threshold (e.g., 0.5, 0.7, between 0.4 and 0.8, etc.), which forms the segmentation.

The probability threshold can optionally be dependent on any number of features of the segmentation and/or images, such as any or all of: the location of the segmented region (e.g., intraparenchymal, intraventricular, epidural, subdural, subarachnoid, etc.), the suspected condition (e.g., and a severity of the condition being tested for), metadata, and/or any other suitable features. Alternatively, the probability threshold can be constant.

Additionally or alternatively, probabilities from multiple voxels can be aggregated (e.g., averaged) and compared with a threshold, a minimum number of high probabilities can need to be reached, and/or any probabilities can be examined in any suitable ways.

Further additionally or alternatively, the method can be performed in absence of determining a probability score S220 can optionally include evaluating one or more exclusion criteria in the image data (e.g., potential affected brain region, segmented brain region, etc.), which can function to verify that the image data is relevant for evaluation in the rest of the method, save time and/or resources by eliminating irrelevant scans, check for a particular set of false positives (e.g., artifacts, eliminate one or more categories of false positives while still maintaining an overall high percentage of false negatives, minimizing a number of false positives, eliminating one or more categories of false positives while still maintaining an overall high percentage of false positives, etc.), route a set of instances corresponding to one or more exclusion criteria to another workflow in a healthcare facility, or perform any other suitable function. In some variations, for instance, a set of exclusion criteria are evaluated, which function to keep "close call" false positives (e.g., questionable pathologies, affected brain tissue, etc.) while eliminating false positives caused by non-physiological events (e.g., metal artifact, poor image quality, etc.). Additionally or alternatively, exclusion criteria are evaluated to minimize an overall number of false positives, thereby minimizing, for instance, unnecessary interruptions to specialists and/or any other number of recipients (e.g., clinical trial principal investigators). Alternatively, the method can partially or fully process all sets of instances.

Evaluating exclusion criteria preferably includes checking for any or all of: the presence of an artifact in one or more of the set of instances (e.g., metallic artifact, aneurysm clip, etc.), improper timing at which the set of instances were taken at an imaging modality (e.g., premature timing, improper timing of a bolus, etc.), one or more incomplete regions (e.g., features, anatomical features, etc.) in the set of instances (e.g., incomplete skull, incomplete vessel, incomplete soft matter region, etc.), an incorrect scan type or body part (e.g., non-head CT scan, non-contrast CT scan, etc.), poor image quality (e.g., blurry images, low contrast, etc.), movement of the patient during the scan (e.g., manifesting as bright streaks in one or more images), a calcification, or any other suitable exclusion criteria.

In one variation, a set of images (e.g., instances, series, etc.) are evaluated to determine if an artifact is present, wherein the set of images is excluded from further processing if an artifact is found. In a specific example, the method includes inspecting the HU values of voxels in a soft matter mask, wherein voxels having a value above a predetermined threshold (e.g., 3000 HU, between 2000 and 4000 HU, etc.) are determined to be a metallic artifact (e.g., aneurysm clip).

Checking for exclusion criteria can optionally additionally or alternatively include comparing a size of a region with a size criteria, wherein connected components (e.g., segmentations) are evaluated based on any or all of: area (e.g., number of pixels), volume (e.g., volume in mL, number of voxels etc.), one or more characteristic dimensions (e.g., maximum dimension, minimum dimension, length, width, maximum length, maximum width, thickness, radius, diameter, etc.), or any other suitable size category. The size can be compared with a threshold, wherein if the size is below the threshold (e.g., indicating an artifact, indicating noise, etc.), the component is eliminated from further processing and/or consideration. Additionally or alternatively, if the size is above a threshold (e.g., indicating an image quality issue, indicating an ischemic core condition too severe for intervention, indicating the patient moving during the scan, etc.), the component can be eliminated from further processing and/or consideration; if the size is within a range of thresholds, the component can be eliminated from further processing and/or consideration; if the size is outside a range of thresholds, the component can be eliminated from further processing and/or consideration; or the component can be otherwise evaluated and/or further processed (e.g., evaluated to determine an ischemic core vs. an ischemic penumbra).

In some variations, for instance, a size of the segmented region is compared with a minimum volume threshold, wherein if the segmented region size is below the minimum volume threshold, the segmented region is eliminated from further consideration of the condition, and wherein if the segmented region size is above the minimum volume threshold, the segmented region continues to further processing and/or results in the determination of the suspected condition. Additionally or alternatively, the size threshold can include a 2D size threshold (e.g., per slice), 1D size threshold (e.g., largest length of segmentation in a slice, largest width of segmentation in a slice, thickness, etc.), and/or any other suitable thresholds.

Checking for exclusion criteria can optionally further additionally or alternatively include comparing a location of the region with a location criteria, wherein connected components (e.g., segmentations) are evaluated based on their proximity to another component, such as another anatomical component (e.g., bone, skull, etc.), a particular brain region or brain feature (e.g., particular sulcus, lobe, covering, etc.), an image feature (e.g., an image edge, etc.), or any other component or general location. In the event that the relative location (e.g., distance, proximity, etc.) is below a threshold (indicating that the component is too close), the component can be discarded.

The condition typically refers to a hypothesized patient condition or diagnosis (e.g., ischemic core, ICH, LVO, aneurysm, stroke, etc.) but can additionally or alternatively include a severity (e.g., based on a predetermined severity scale), an urgency, or any other characteristic.

S220 preferably produces as an output a determination of a patient condition, wherein this determination can trigger one or more outcomes (e.g., as described below), prompt further analysis (e.g., the determination of one or more associated parameters), be recorded (e.g., in a patient record), and/or be otherwise used. In variations of ischemic core, for instance, further analysis can be triggered to determine any or all of: an amount of affected (e.g., compromised) brain, an amount of unaffected brain, the particular affected region (e.g., brain territory, brain lobe, etc.), the function of the affected region (e.g., motor control, memory, emotion, etc.), a trajectory of the affected region (e.g., rate of spreading, blood flow rate, etc.), or any other suitable parameter.

In one variation, S220 includes: receiving image data including a brain image and its mirror image (e.g., individually, in an overlaid fashion, individually after being registered in an overlaid fashion, etc.); segmenting a region of the image data (e.g., in the brain image, in an overlaid image, etc.) indicating a potential ischemia (e.g., early ischemia) with a CNN (e.g., V-net, U-net, etc.); and determining the suspected condition based on the segmentation (e.g., based on a size of the region in comparison with one or more volume thresholds, based on an aggregated probability score, based on a binary presence of a segmentation, etc.). Additionally or alternatively, S220 can include comparing one or more parameters (e.g., HU value, pixel value, number of pixels, length, etc.) of the segmented region with its overlapping region in the mirror image (e.g., corresponding region in the opposing hemisphere); and determining a potential ischemia based on this comparison (e.g., exceeds the corresponding parameter by a predetermined threshold, the corresponding parameter exceeds its value by a predetermined threshold, etc.). In a specific example, for instance, S220 includes identifying a relatively dark region in a left hemisphere of an image; identifying the corresponding region in the right hemisphere based on the registered overlaid image; determining a darkness associated with this corresponding region; comparing the two darknesses and determining that the left hemisphere region's darkness exceeds the corresponding right hemisphere region's darkness by a predetermined threshold; and determining that the patient is potentially experiencing an ischemic core condition.

4.5 Method—in an Event that the Suspected Condition is Detected, Determining a Recipient Based on the Suspected Condition S230

The method includes in an event that the suspected condition is detected, determining a recipient based on the suspected condition S230, which functions to facilitate the treatment (e.g., triage, acceptance into a clinical trial, etc.) of the patient.

S230 can additionally, alternatively, and/or equivalently include determining a treatment option S230, preferably in the event that a condition is detected (e.g., based on a comparison with a threshold, based on a binary presence, etc.) but can additionally or alternatively determine a treatment option when a condition is not detected, when an analysis is inconclusive, or in any suitable scenario. S230 can function to match the patient with a specialist, initiate the transfer of a patient to a $2^{nd}$ point of care (e.g., specialist facility), initiate the transfer of a specialist to a $1^{st}$ point of care, or initiate treatment of a patient (e.g., surgery, stent placement, mechanical thrombectomy, etc.) within the $1^{st}$ point of care, initiate the matching of a patient to a clinical trial, or perform any other suitable function. In some variations, the treatment option is a $2^{nd}$ point of care, wherein it is determined (e.g., suggested, assigned, etc.) that the patient should be treated at the $2^{nd}$ point of care. Additionally or alternatively, the treatment option can be a procedure (e.g., surgical procedure, surgical clipping, mechanical thrombectomy, placement of an aneurysm coil, placement of a stent, retrieval of a thrombus, stereotactic radiosurgery, etc.), treatment (e.g., tissue plasminogen activator (TPA), pain killer, blood thinner, etc.), recovery plan (e.g., physical therapy, speech therapy, etc.), or any other suitable treatment.

The recipient and/or treatment is preferably determined based on a parameter determined from the data packet (e.g., binary presence of a condition, comparison of a parameter with a threshold, etc.), but can additionally or alternatively be determined based on additional data, such as patient information (e.g., demographic information, patient history, patient treatment preferences, etc.), input from one or more individuals (e.g., power of attorney, attending physician, emergency physician, etc.), a consensus reached by multiple recipients of a notification (e.g., majority of members of a care team, all members of a care team, etc.), or any other suitable information.

S230 is preferably at least partially performed with software operating at the remote computing system (e.g., remote server) but can additionally or alternatively be performed at a remote computing system separate from a previous remote computing system, a local computing system (e.g., local server, virtual machine coupled to healthcare facility server, computing system connected to a PACS server), or at any other location.

S230 is preferably performed after a patient condition has been determined during the method 200. Additionally or alternatively, S230 can be performed after a patient condition has been determined in an alternative workflow (e.g., at the $1^{st}$ point of care, at a radiologist workstation during a standard radiology workflow, in the case of a false negative, etc.), prior to or absent the determination of a patient condition (e.g., based on an input from a healthcare worker at the remote computing system, when patient is admitted to $1^{st}$ point of care, etc.), multiple times throughout the method (e.g., after a first treatment option fails, after a first specialist is unresponsive, such as after a threshold amount of time, such as 30 seconds, 1 minute, 2 minutes, etc.), or at any other time during the method.

S230 preferably determines a recipient (and/or a treatment option) with a lookup table located in a database accessible at remote computing system (e.g., cloud-computing system). Additionally or alternatively, a lookup table can be stored at a healthcare facility computing system (e.g., PACS server), in storage at a user device, or at any other location.

In other variations, the recipient and/or treatment option can be determined based on one or more algorithms (e.g., predictive algorithm, trained algorithm, etc.), one or more individuals (e.g., specialist, care team, clinical trial coordinator, etc.), a decision support tool, a decision tree, a set of mappings, a model (e.g., deep learning model), or through any other process or tool.

The lookup table preferably correlates a $2^{nd}$ point-of-care (e.g., healthcare facility, hub, physician, specialist, neuro-interventionist, etc.), further preferably a specialist or contact (e.g., administrative worker, emergency room physician, etc.) associated with the $2^{nd}$ point of care, with a patient condition (e.g., presence of an LVO, presence of a pathology, severity, etc.), but can additionally or alternatively correlate a treatment option with the patient condition, and/or any other suitable recipient (e.g., at a $1^{st}$ point of care, associated with a clinical trial, etc.) with the condition. The lookup table can further additionally or alternatively correlate a treatment option with supplementary information (e.g., patient history, demographic information, heuristic information, etc.).

The recipient, equivalently referred to herein as contact, (e.g., healthcare provider, neuro-interventional specialist, principal investigator, stroke care team member, clinical trial enrollment committee, etc.) is preferably a healthcare worker, but can additionally or alternatively be any individual associated with the treatment of the patient and/or be associated with any healthcare facility (e.g., prior healthcare facility of patient, current healthcare facility, recommended healthcare facility) related to the patient. The contact is further preferably a specialist (e.g., neuro-interventional specialist, neurosurgeon, neurovascular surgeon, general surgeon, cardiac specialist, etc.) but can additionally or alternatively include an administrative worker associated with a specialist, multiple points of contact (e.g., ranked order, group, etc.), or any other suitable individual or group of individuals. The contact is preferably associated with a hub facility, wherein the hub facility is determined as an option for second point of care, but can additionally or alternatively be associated with a spoke facility (e.g., current facility, future facility option, etc.), an individual with a relation to the patient (e.g., family member, employer, friend, acquaintance, emergency contact, etc.), or any other suitable individual or entity (e.g., employer, insurance company, etc.). Additionally or alternatively, the contact can be an individual associated with a clinical trial (e.g., principal investigator at a $1^{st}$ point of care, principal investigator at a $2^{nd}$ point of care, approval/enrollment committee to approve a patient for a clinical trial, etc.), and/or any other suitable individual.

The lookup table is preferably determined based on multiple types of information, such as, but not limited to: location information (e.g., location of a $1^{st}$ point of care, location of a $2^{nd}$ point of care, distance between points of care, etc.), temporal information (e.g., time of transit between points of care, time passed since patient presented at $1^{st}$ point of care, etc.), features of condition (e.g., size of occlusion, severity of condition, etc.), patient demographics (e.g., age, general health, history, etc.), specialist information (e.g., schedule, on-call times, historic response time, skill level, years of experience, specialty procedures, historic success or procedures, etc.), healthcare facility information (e.g., current number of patients, available beds, available machines, etc.), but can additionally or alternatively be determined based on a single type of information or in any other suitable way. Information can be actual, estimated, predicted, or otherwise determined or collected.

In some variations, the method 200 includes transmitting information (e.g., patient condition, data determined from analysis, optimal set of instances, series, data packet, etc.) to the computing system associated with the lookup table.

4.6 Method—Preparing a Data Packet for Transfer S240

The method 200 can include preparing a data packet for transfer, which can function to produce a compressed data packet, partially or fully anonymize a data packet (e.g., to comply with patient privacy guidelines, to comply with Health Insurance Portability and Accountability Act (HIPAA) regulations, to comply with General Data Protection Regulation (GDRP) protocols, etc.), minimize the time to transfer a data packet, annotate one or more images, or perform any other suitable function. Additionally or alternatively, any or all of a data packet previously described can be transferred.

The data packet is preferably transferred (e.g., once when data packet is generated, after a predetermined delay, etc.) to a contact, further preferably a specialist (e.g., associated with a $2^{nd}$ point of care, located at the $1^{st}$ point of care, etc.), but can additionally or alternatively be sent to another healthcare facility worker (e.g., at $1^{st}$ point of care, radiologist, etc.), an individual (e.g., relative, patient, etc.), a healthcare facility computing system (e.g., workstation), a server or database (e.g., PACS server), or to any other suitable location.

S240 preferably includes compressing a set of images (e.g., series), but can additionally or alternatively leave the set of images uncompressed, compress a partial set of images (e.g., a subset depicting the condition), or compress any other part of a data packet. Compressing the data packet functions to enable the data packet to be sent to, received at, and viewed on a user device, such as a mobile device. Compressing the data packet can include any or all of: removing a particular image region (e.g., region corresponding to air, region corresponding to hard matter, region without contrast dye, irrelevant anatomical region, etc.), thresholding of voxel values (e.g., all values below a predetermined threshold are set to a fixed value, all values above a predetermined threshold are set to a fixed value, all values below −500 HU are set to −500, all voxel values corresponding to a particular region are set to a fixed value, all voxels corresponding to air are set to a predetermined fixed value, etc.), reducing a size of each image (e.g., scale image size by factor of 0.9, scale image size by factor of 0.7, scale image size by factor of 0.5, scale image size by a factor between 0.1 and 0.9, reduce image size by a factor of 4, etc.), or through any other compression method.

In one variation, the reduction in size of a set of images can be determined based on one or more memory constraints of the receiving device (e.g., user device, mobile device, etc.).

In some variations, such as those involving a patient presenting with a brain condition (e.g., ischemic core), the images taken at an imaging modality (e.g., CT scanner) are compressed by determining an approximate or exact region in each image corresponding to air (e.g., based on HU value, based on location, based on volume, etc.) and setting the air region (e.g., voxels corresponding to the air region, pixels corresponding to the air region, etc.) to have a fixed value. Additionally or alternatively, any non-critical region (e.g., bone, unaffected region, etc.) or other region can be altered (e.g., set to a fixed value, removed, etc.) during the compression. In a specific example, for instance, a set of voxels corresponding to air are set to all have a common fixed value (e.g., an upper limit value, a lower limit value, a value between 0 and 1, a predetermined value, etc.).

In some variations, S240 includes identifying an optimal visualization to be transmitted (e.g., from a remote computing system) and received (e.g., at a user device), which functions to prepare an optimal output for a $2^{nd}$ point of care (e.g., specialist), reduce the time required to review the data packet, bring attention to the most relevant image data, or to effect any other suitable outcome.

In some variations, this involves a reverse registration process. In a specific example, for instance, this is done through maximum intensity projection (MIP), where an optimal range of instances is determined based on which images contain the largest percentage of the segmented anatomical region of interest in a MIP image.

Additionally or alternatively, S240 can include removing and/or altering (e.g., encrypting) metadata or any unnecessary, private, confidential, or sensitive information from the data packet. In some variations, patient information (e.g., patient-identifiable information) is removed from the data packet in order to comply with regulatory guidelines. In other variations, all metadata are extracted and removed from the data packet.

S240 can optionally include annotating one or more images in the data packet, which can function to draw attention to one or more features of the images, help a specialist or other recipient easily and efficiently assess the images, and/or perform any other suitable functions.

Annotating the images can optionally include adding (e.g., assigning, overlaying, etc.) one or more visual indicators (e.g., labels, text, arrows, highlighted or colored regions, measurements, etc.) to one or more images. The incorporation of the visual indicators can be determined based on any or all of: the suspected condition (e.g., type of visual indicators designated for the condition based on a lookup table), one or more thresholds (e.g., size thresholds), features of the suspected condition/pathology (e.g., ischemic penumbra vs. ischemic core, location of condition within brain, etc.), preferences (e.g., specialist preferences, point of care preferences, etc.), guidelines (e.g., patient privacy guidelines), the results of one or more deep learning models, and/or any other suitable factors or information. In variations with visual indicators, a table/key can optionally be provided to explain the visual indicators, which can include any or all of: a color key defining what colors correspond to; one or more parameters associated with an indicated region or feature (e.g., volume of core); one or more parameters associated with the image(s) as a whole (e.g., total volume measured across all regions, number of regions indicated, etc.); and/or any other suitable information.

Images can additionally or alternatively be annotated with one or more metrics, such as one or more parameters (e.g., size as described above); scores (e.g., a clinical score, a severity score, etc.); instructions (e.g., recommended intervention); and/or any other suitable information.

Additionally or alternatively to being annotated on an image, any or all of the annotations can be provided in a separate notification, such as a message, document, and/or provided in any other suitable way.

The annotations are preferably determined automatically (e.g., at a remote computing system implementing the deep learning models, at a client application, at a mobile device executing a client application, etc.), but can additionally or alternatively be determined manually, verified manually, or otherwise determined.

In some variations, for instance, a size (e.g., volume) of the affected area (e.g., ischemia, ischemic core, etc.) has been found to be helpful in decision-making for the specialist (e.g., determining whether or not to intervene, determining a type of intervention, etc.) and is indicated to the specialist on one or more images transmitted to him or her. In specific examples, the region is indicated by (e.g., highlighted in, outlined in, etc.) one of a set of colors, wherein the color can indicate any or all of: a type of ischemia, a calculated size (e.g., volume) of the affected region, and/or any other suitable information.

S240 can optionally include prescribing a subset of images to be viewed by the recipient and/or an order in which images should be viewed (e.g., the particular image shown first to the recipient upon opening a client application in response to receiving a notification, the image shown in the thumbnail of a notification, the only image or subset of images sent, etc.). This can include, for instance, selecting the image or images indicating the suspected condition (e.g., all slices containing the suspected condition, a single slice containing the suspected condition, the slice containing the largest cross section of a suspected condition, the slice containing an important or critical feature of the suspected condition, etc.) for viewing by the recipient. In specific examples, the recipient (e.g., specialist) is sent a notification wherein when the recipient opens the notification on a device (e.g., mobile device), the image corresponding to the suspected condition is shown first (and optionally corresponds to a thumbnail image shown to the recipient in the notification).

The notification(s) and/or image(s) provided to a recipient are preferably provided within a threshold time period from the time in which the patient is imaged (e.g., 15 minutes, between 10 and 15 minutes, 10 minutes, 9 minutes, 8 minutes, 7 minutes, 6 minutes, 5 minutes, 3 minutes, 2 minutes, 1 minute, etc.), but can additionally or alternatively be provided in another suitable time frame (e.g., greater than 15 minutes), prior to a next action in the standard of care (e.g., prior to a decision is made by a radiologist in a parallel workflow), and/or at any other time(s).

In some variations, S240 includes storing a dataset (e.g., at a remote server, at a local server, at a PACS server, etc.). In one example, metadata are extracted from the image data and stored separately from image data in a relational database. In another example, any or all of the data packet are stored (e.g., temporarily, permanently, etc.) to be used in one or more future analytics processes, which can function to improve the method, better match patients with suitable treatment options, or for any other suitable purpose.

S240 can optionally include applying a low bandwidth implementation process, which can function to reduce the time until a specialist receives a first piece of data or data packet (e.g., an incomplete series, incomplete study, single instance, single image, optimal image, image showing occlusion, etc.), reduce the processing required to inform a specialist of a potential patient condition, reduce the amount of data required to be reviewed by a specialist, reduce the amount of data being transmitted from a remote computing system to a mobile device, or perform any other suitable function. The low bandwidth implementation process can include any or all of: organizing (e.g., chunking) data (e.g., chunking a series of images based on anatomical region), reordering data (e.g., reordering slices in a CT series), transmitting a portion (e.g., single image, single slice, etc.) of a data packet (e.g., series, study, set of images, etc.) to a device (e.g., user device, mobile device, healthcare facility workstation, computer, etc.), sending the rest of the data packet (e.g., only in response to a request, after a predetermined time has passed, once the data packet has been fully processed, etc.), or any other process. In a specific example, for instance, the image data (e.g., slices) received at a remote computing system from a scanner are chunked, reordered, and a subset of slices (e.g., single slice) is sent to the device associated with a specialist first (e.g., prior to sending a remaining set of slices, in absence of sending a remainder of slices, etc.).

In some variations, S240 includes implementing a buffering protocol, which enables a recipient (e.g., specialist) to start viewing images (e.g., on a mobile device) prior to all of the images being loaded at the device (e.g., user device, mobile device, etc.) at which the recipient is viewing images. Additionally or alternatively, the buffering protocol can include transmitting images to the recipient in batches, annotating images in batches, or otherwise implementing a buffering protocol.

Additionally or alternatively, S240 can include any other suitable steps performed in any suitable order.

The method can additionally or alternatively include any other suitable sub-steps for preparing the data packet.

In a first set of variations, S240 includes determining a subset of one or more images conveying information related to a suspected patient condition (e.g. showing the presence of the condition, showing the largest region of the condition, showing a particular feature of the condition, etc.); optionally annotating the images (e.g., to point out the condition); and preparing a notification to be sent to the specialist, wherein the notification instructs the specialist to view at least the subset of images and optionally includes a thumbnail depicting one of the set of images which the specialist can view prior to viewing the images.

4.7 Method—Transmitting Information to a Device Associated with a Recipient S250

Figure 6:
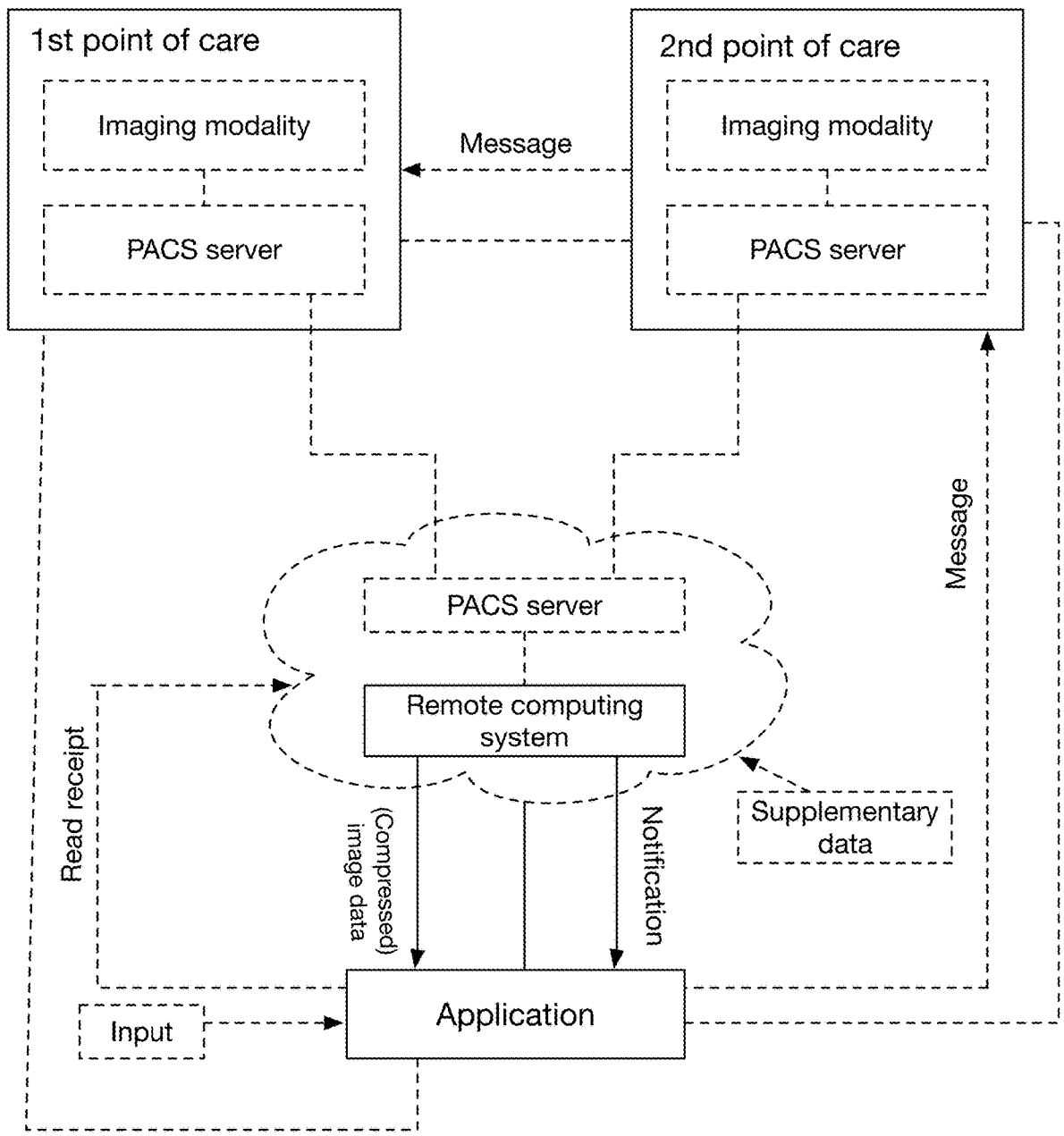
FIG. 6 depicts a variation of a system for computer-aided triage.

Transmitting information to a device associated with a recipient (e.g., at the $1^{st}$ point of care, at a $2^{nd}$ point of care, a specialist, etc.) S250 (e.g., as shown in FIG. 6) can optionally function to initiate a pull from a $1^{st}$ point of care to a $2^{nd}$ point of care, which can decrease time to care, improve quality of care (e.g., better match between patient condition and specialist), or have any other suitable outcome. Preferably, the $2^{nd}$ point of care is a hub facility (e.g., specialist facility, interventional center, comprehensive stroke center, etc.). In some variations, the $1^{st}$ point of care (e.g., healthcare facility at which patient initially presents) also functions as the $2^{nd}$ point of care, such as when a suitable specialist is associated with the $1^{st}$ point of care, the $1^{st}$ point of care is a hub (e.g., specialist facility, interventional center, comprehensive stroke center, etc.), it is not advised to transfer the patient (e.g., condition has high severity), or for any other reason. Additionally or alternatively, S250 can function to enroll a patient in a clinical trial, treat the patient (e.g., at the $1^{st}$ point of care, at a $2^{nd}$ point of care, etc.), and/or perform any other suitable functions.

S250 is preferably performed after a data packet (e.g., compressed data packet, encrypted data packet, etc.) and a recipient have been determined, but can additionally or alternative be performed at any or all of: in response to a $2^{nd}$ point of care being determined, multiple times throughout the method (e.g., to multiple recipients, with multiple data packets, with updated information, after a predetermined amount of time has passed since a notification has been sent to a first choice specialist, etc.), or at any other time during the method 200.

The device is preferably a user device, further preferably a mobile device. Examples of the user device include a tablet, smartphone, mobile phone, laptop, watch, wearable device (e.g., glasses), or any other suitable user device. The user device can include power storage (e.g., a battery), processing systems (e.g., CPU, GPU, memory, etc.), user outputs (e.g., display, speaker, vibration mechanism, etc.), user inputs (e.g., a keyboard, touchscreen, microphone, etc.), a location system (e.g., a GPS system), sensors (e.g., optical sensors, such as light sensors and cameras, orientation sensors, such as accelerometers, gyroscopes, and altimeters, audio sensors, such as microphones, etc.), data communication system (e.g., a WiFi module, BLE, cellular module, etc.), or any other suitable component.

The device is preferably associated with (e.g., owned by, belonging to, accessible by, etc.) a specialist or other individual associated with the $2^{nd}$ point of care, but can additionally or alternatively be associated with an individual or computing system at the $1^{st}$ point of care, the patient, a clinical trial, or any other suitable individual or system.

In one variation, the device is a personal mobile phone of a specialist. In another variation, the device is a workstation at a healthcare facility (e.g., first point of care, second point of care, etc.).

In some variations, information is sent to multiple members (e.g., all members) of a care team or clinical trial team, such as the care team who is treating, may treat the patient, or and/or will treat the patient. This can enable the care team members to do any or all of: make a decision together (e.g., transfer decision, treatment decision, etc.); communicate together (e.g., through the client application); and/or perform any other function.

The information preferably includes a data packet, further preferably the data packet prepared in S240. Additionally or alternatively, the information can include a subset of a data packet, the original data packet, any other image data set, or any other suitable data. The information further preferably includes a notification, wherein the notification prompts the individual to review the data packet at the device (e.g., a message reciting "urgent: please review!"). The notification can optionally include a thumbnail with a selected image (e.g., image indicating patient condition), which a recipient can view quickly, such as prior to the recipient unlocking device to which the notification is sent. Additionally or alternatively, the notification can prompt the individual to review data (e.g., original data packet, uncompressed images, etc.) at a separate device, such as a workstation in a healthcare facility, a PACS server, or any other location. Further additionally or alternatively, the notification can include any suitable information, such as, but not limited to: instructions (e.g., for treating patient, directions for reaching a healthcare facility), contact information (e.g., for emergency physician at first point of care, administrative assistant, etc.), patient information (e.g., patient history), or any other suitable information.

The notification preferably includes an SMS text message but can additionally or alternatively include a message through a client application (e.g., as described above, image viewing application, medical imaging application, etc.), an email message (e.g., de-identified email), audio notification or message (e.g., recording sent to mobile phone), push notification, phone call, a notification through a medical platform (e.g., PACS, EHR, EMR, healthcare facility database, etc.), or any other suitable notification.

One or more features of a notification can optionally convey a severity of the patient condition and/or an urgency of receiving a response from a recipient, which can function to adequately alert the recipient and properly prioritize care of the patient (e.g., relative to other patients). In specific examples, for instance, an audio cue associated with a notification indicates an urgency of treating a patient, so that a recipient of the message knows to immediately review the images and triage the patient.

The information is preferably sent to the device through a client application executing on the user device but can additionally or alternatively be sent through a messaging platform, web browser, or other platform. In some variations, the information is sent to all devices (e.g., mobile phone, smart watch, laptop, tablet, workstation, etc.) associated with the recipient (e.g., specialist), such as all devices executing the client application associated with the recipient, which functions to increase the immediacy in which the recipient is notified.

Figure 10:
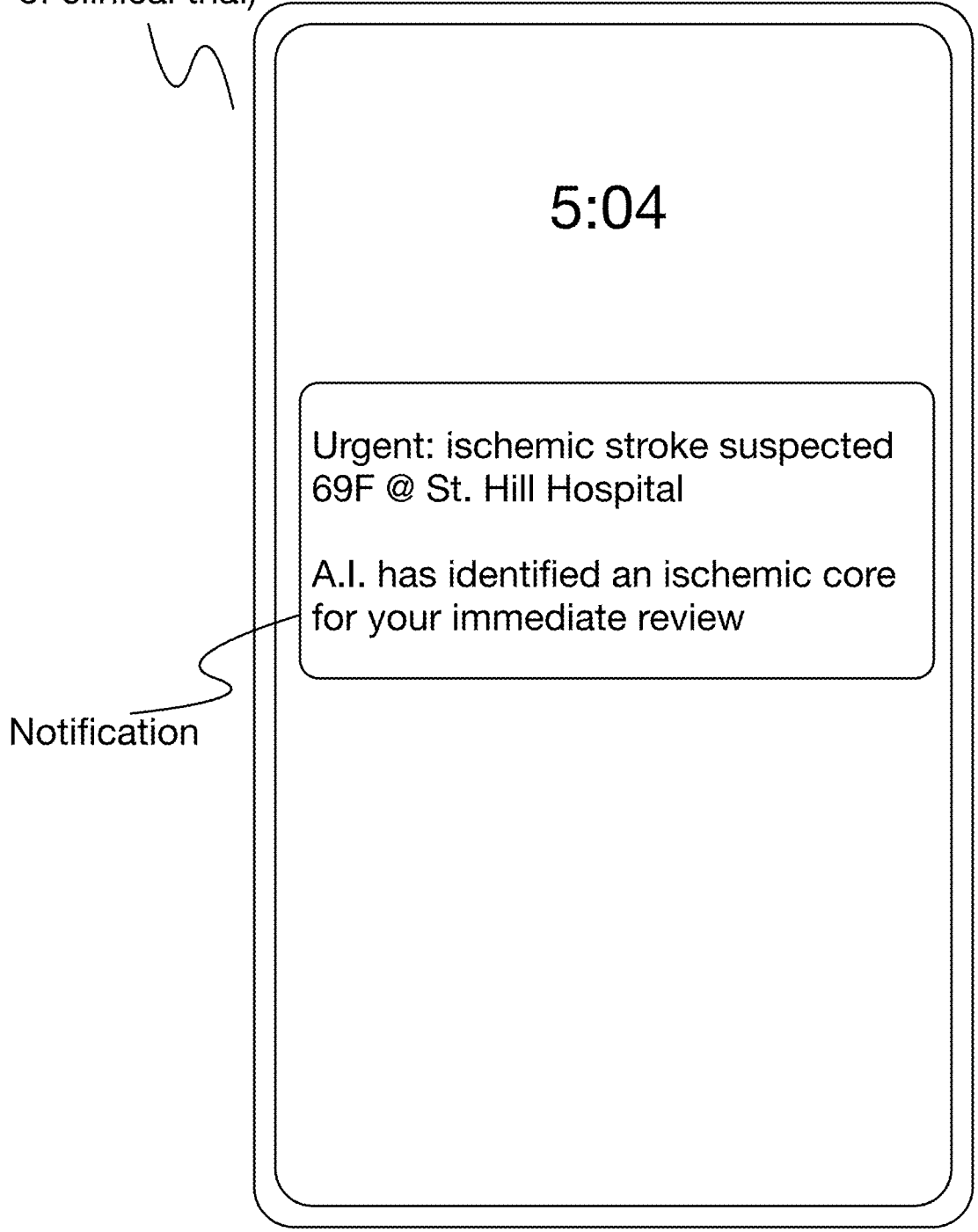
FIG. 10 depicts a variation of a notification transmitted to a device of a recipient.

In one variation, S240 and S250 include preparing a notification to be sent to a device (e.g., user device, mobile device, etc.) associated with a recipient (e.g., a specialist), wherein the notification includes a thumbnail (e.g., as shown in FIG. 10) indicating a selected image (e.g., compressed image showing a suspected condition), along with a message instructing the recipient to review the images in a client application, and optionally the original images at a workstation afterward. In a first set of specific examples, upon detection that a read receipt has not been received (e.g., at the remote computing system) in a predetermined amount of time (e.g., 30 seconds, 1 minute, 2 minutes, between 0 seconds and 2 minutes, 3 minutes, between 2 minutes and 3 minutes, 5 minutes, greater than 5 minutes, less than 10 minutes, etc.), a second notification is transmitted to a second recipient (e.g., a second specialist). In a second set of specific examples, sending the notification further triggers and/or enables communication to be established among multiple members of a care team (e.g., a stroke team), such as through a messaging component of the client application, wherein the images can be viewed and discussed among the care team members. In a third set of specific examples, a notification is sent to specialist on a mobile device of the specialist, compressed images are previewed on the specialist mobile device, and the specialist is notified as being responsible for viewing non-compressed images on a diagnostic viewer and engaging in appropriate patient evaluation and relevant discussion with a treating physician before making care-related decisions or requests.

In a second variation, S240 and S250 include preparing a notification to be sent to a clinical trial research coordinator, such as a principal investigator, wherein the notification indicates that the patient is a potential candidate for a clinical trial (e.g., based on the detection of a suspected condition, based on a set of clinical trial inclusion criteria, etc.). In specific examples, a notification can be sent (e.g., automatically, triggered by the principal investigator, etc.) to a members of a clinical trial committee (e.g., physician committee), wherein approval is granted by the committee members (e.g., a majority, all, at least one, a predetermined number or percentage, etc.), such as through the client application.

A notification can optionally be sent which prompts the individual to provide an input, wherein the input can indicate that the individual will view, has viewed, or is in the process of viewing the information (e.g., image data), sees the presence of a condition (e.g., true positive, serious condition, time-sensitive condition, etc.), does not see the presence of a condition (e.g., false positive, serious condition, time-sensitive condition, etc.), has accepted treatment of the patient (e.g., swipes right, swipes up, clicks a check mark, etc.), has denied treatment of the patient (e.g., swipes left, swipes down, clicks an 'x', etc.), wants to communicate with another individual (e.g., healthcare worker at $1^{st}$ point of care), such as through a messaging platform (e.g., native to the device, enabled by the client application, etc.), or any other input. In some variations, one or more additional notifications are provided to the individual (e.g., based on the contents of the input), which can be determined by a lookup table, operator, individual, decision engine, or other tool. In one example, for instance, if the individual indicates that the condition is a true positive, information related to the transfer of the patient (e.g., estimated time of arrival, directions to the location of the patient, etc.) can be provided (e.g., in a transfer request, wherein patient transfer to a specified location, such as the $2^{nd}$ point of care, can be initiated upon transfer request receipt). In some variants, the data (e.g., images) are displayed on the user device (e.g., mobile device, workstation) in response to user interaction with the notification (e.g., in response to input receipt). However, the input can trigger any suitable action or be otherwise used.

Additionally or alternatively, an input can automatically be received from the client application, such as a read receipt when the individual has opened the data packet, viewed the notification, or interacted with the client application in any other suitable way. In one example, if a read receipt is not received (e.g., at the remote computing system) from the device within a predetermined amount of time (e.g., 10 seconds), a second notification and/or data packet (e.g., compressed set of images) are sent to a second individual (e.g., second choice specialist based on a lookup table).

In some variations, various outputs can be sent from the client application (e.g., at the user device) to one or more recipients (e.g., to a second user device, client application on a work station, on a computing system, etc.), such as recipients associated with a first point of care (e.g., radiologists, emergency physicians, etc.). The outputs can be determined based on the inputs received at the client application associated with the individual (e.g., acceptance of case, verification of true positive, etc.), based on a lookup table, or otherwise determined. The outputs preferably do not alter the standard radiology workflow (e.g., are not shared with radiologists; radiologists are not notified), which functions to ensure that the method 200 is a true parallel process, and that the standard radiology workflow results in an independent assessment of the patient, but can additionally or alternatively cut short a workflow, bring a specialist in on the patient case earlier than normal, or affect any other process in a healthcare facility.

The method can additionally or alternatively include initiating the transfer of a patient, wherein the transfer includes a recommendation that the patient be considered for a clinical and/or research trial, based on one or more of: a suspected clinical condition of the patient (e.g., ischemic core), patient information (e.g., demographic information), a patient's willingness or potential willingness to participate, and/or any other suitable information. Initiating the recommendation can include transmitting any or all of the notifications described above (e.g., text message, call, email, etc.) to a specialist involved in the clinical and/or research trial, a specialist who has actively turned on notifications for clinical trial recruitment, a researcher, a research principal investigator, an administrative assistant, the patient himself, or any other suitable entity or individual.

4.8 Method—Receiving an Input from the Recipient

The method 200 can include receiving an input from the recipient, which functions to determine a next step for the patient, and can include any or all of: a confirmation of the suspected condition; a rejection of the suspected condition (e.g., false positive); an acceptance by a specialist and/or care team (e.g., stroke team) to treat the patient (e.g., at a $1^{st}$ point of care, at a $2^{nd}$ point of care, etc.); a rejection of a specialist and/or care team to treat the patient; a read receipt and/or an indication of a lack or a read receipt within a predetermined time threshold; an approval to enroll the patient in a clinical trial; and/or any other suitable input.

In some variations, a notification is sent in S250 which prompts the individual to provide an input, wherein the input can indicate that the individual will view, has viewed, or is in the process of viewing the information (e.g., image data), sees the presence of a condition (e.g., true positive, serious condition, time-sensitive condition, etc.), does not see the presence of a condition (e.g., false positive, serious condition, time-sensitive condition, etc.), has accepted treatment of the patient (e.g., swipes right, swipes up, clicks a check mark, etc.), has denied treatment of the patient (e.g., swipes left, swipes down, clicks an 'x', etc.), wants to communicate with another individual (e.g., healthcare worker at $1^{st}$ point of care), such as through a messaging platform (e.g., native to the device, enabled by the client application, etc.), or any other input. In some variations, one or more additional notifications are provided to the individual (e.g., based on the contents of the input), which can be determined by a lookup table, operator, individual, decision engine, or other tool. In one example, for instance, if the individual indicates that the condition is a true positive, information related to the transfer of the patient (e.g., estimated time of arrival, directions to the location of the patient, etc.) can be provided (e.g., in a transfer request, wherein patient transfer to a specified location, such as the $2^{nd}$ point of care, can be initiated upon transfer request receipt). In some variants, the data (e.g., images) are displayed on the user device (e.g., mobile device, workstation) in response to user interaction with the notification (e.g., in response to input receipt). However, the input can trigger any suitable action or be otherwise used.

Additionally or alternatively, an input can automatically be received from the client application, such as a read receipt when the individual has opened the data packet, viewed the notification, or interacted with the client application in any other suitable way. In one example, if a read receipt is not received (e.g., at the remote computing system) from the device within a predetermined amount of time (e.g., 10 seconds), a second notification and/or data packet (e.g., compressed set of images) are sent to a second individual (e.g., second choice specialist based on a lookup table).

In some variations, various outputs can be sent from the client application (e.g., at the user device) to one or more recipients (e.g., to a second user device, client application on a work station, on a computing system, etc.), such as recipients associated with a first point of care (e.g., radiologists, emergency physicians, etc.). The outputs can be determined based on the inputs received at the client application associated with the individual (e.g., acceptance of case, verification of true positive, etc.), based on a lookup table, or otherwise determined. The outputs preferably do not alter the standard radiology workflow (e.g., are not shared with radiologists; radiologists are not notified), which functions to ensure that the method 200 is a true parallel process, and that the standard radiology workflow results in an independent assessment of the patient, but can additionally or alternatively cut short a workflow, bring a specialist in on the patient case earlier than normal, or affect any other process in a healthcare facility.

The outputs can include any or all of: the suspected condition, parameters (e.g., volume of an ischemic core) and/or scores (e.g., severity score, urgency score, etc.) associated with the suspected condition; the selection of one or more recipients of a notification (e.g., established and/or proposed care team of the patient); a proposed and/or confirmed intervention for the patient (e.g., type of procedure); an updated status (e.g., location, health status, intervention status, etc.) of one or more patients (e.g., a centralized list of all patients being reviewed by and/or treated by a specialist; a consent of the patient (e.g., for a clinical trial); an estimated parameter of the patient (e.g., estimated time of arrival at a second point of care); and/or any other suitable outputs.

4.9 Method—Initiating Treatment of the Patient

The method can additionally or alternatively include initiating treatment (e.g., transfer) of the patient, wherein the treatment can include any or all of the treatment options described above, such as ay or all of: a point of care (e.g., remain at $1^{st}$ point of care, be transferred to a $2^{nd}$ point of care, etc.) at which the patient will be treated; a procedure to treat the suspected condition; a specialist and/or care team to be assigned to the patient; a clinical trial in which to enroll the patient; and/or any other suitable treatments.

In variations involving recommending the patient for a clinical trial, initiating treatment of the patient can include receiving a recommendation that the patient be considered for a clinical and/or research trial, based on one or more of: a suspected clinical condition of the patient (e.g., ischemic core, ischemic penumbra, etc.), patient information (e.g., demographic information), a patient's willingness or potential willingness to participate, and/or any other suitable information. Initiating the recommendation can include transmitting any or all of the notifications described above (e.g., text message, call, email, etc.) to a specialist involved in the clinical and/or research trial, a specialist who has actively turned on notifications for clinical trial recruitment, a researcher, a research principal investigator, an administrative assistant, the patient himself, or any other suitable entity or individual.

4.8 Method—Aggregating Data S260

The method 200 can optionally include any number of sub-steps involving the aggregation of data involved in and/or generated during the method 200, which can function to improve future iterations of the method 200 (e.g., better match patients with a specialist, decrease time to treat a patient, increase sensitivity, increase specificity, etc.). The aggregated data is preferably used in one or more analytics steps (e.g., to refine a treatment option, make a recommendation for a drug or procedure, etc.), but can additionally or alternatively be used for any other suitable purpose.

In some variations, for instance the outcomes of the patients examined during the method 200 are recorded and correlated with their corresponding data packets, which can be used to assess the success of the particular treatment options chosen and better inform treatment options in future cases.

5. Variations

In one variation of the system 100, the system includes a router 110, which operates at a computing system at a $1^{st}$ point of care and receives image data from an imaging modality. The router transmits the image data to a remote computing system, wherein a series of algorithms (e.g., machine learning algorithms) are performed at the remote computing system, which determines a hypothesis for whether or not a suspected condition (e.g., ICH) is present based on the image data and/or any associated metadata. Based on the determination, a contact is determined from a lookup table (e.g., in storage at the remote computing system), wherein the contact is notified at a user device (e.g., personal device) and sent image data through a client application executing on the user device. One or more inputs from the contact at the application can be received at the remote computing system, which can be used to determine a treatment option (e.g., next point of care) for the patient. However, the system and/or components thereof can be used in any other suitable manner.

In a first variation of the method 200, the method operates in parallel with a standard radiology workflow, which can include any or all of: at a remote computing system (e.g., remote from the first point of care), receiving a set of images (e.g., of a brain of the patient), wherein the set of images is concurrently sent to the standard radiology workflow operating in parallel with the method and automatically detecting a condition (e.g., ischemic core, early signs of ischemic core, etc.) from the set of images. Upon condition detection, the method can include any or all of, automatically: determining a second specialist from the standard radiology workflow, wherein the specialist is associated with a second point of care; notifying the second specialist on a mobile device associated with the second specialist before the radiologist notifies the first specialist; displaying a compressed version of the set of images on the mobile device; and initiating a pull of the patient (e.g., from the $1^{st}$ point of care to the $2^{nd}$ point of care, from the $1^{st}$ point of care to a clinical trial at a later date, as initiated by a specialist at the $2^{nd}$ point of care, as initiated by a specialist at the $1^{st}$ point of care, etc.).

Figure 7:
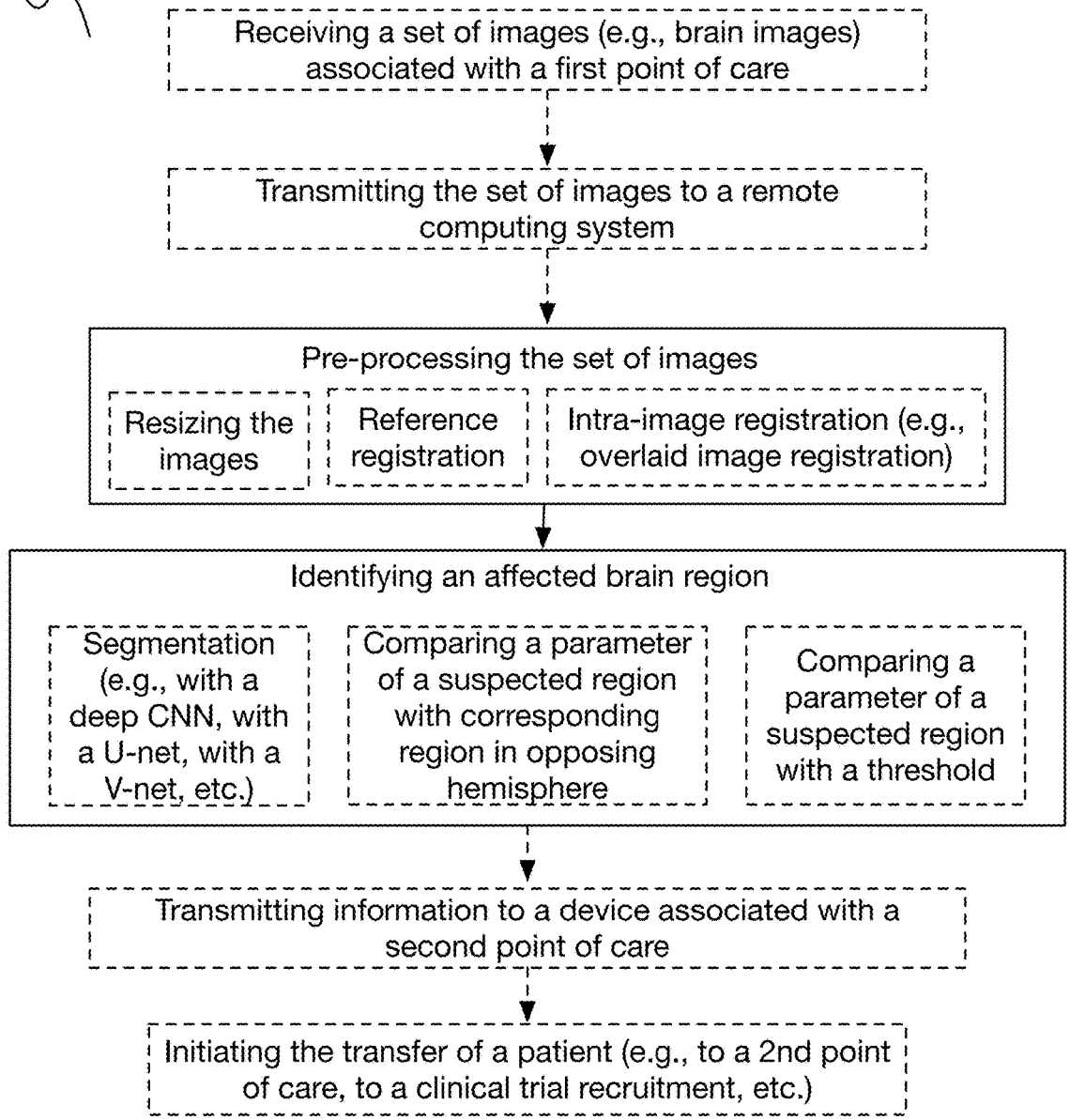
FIG. 7 depicts a variation of a method for computer-aided triage.
Figure 8:
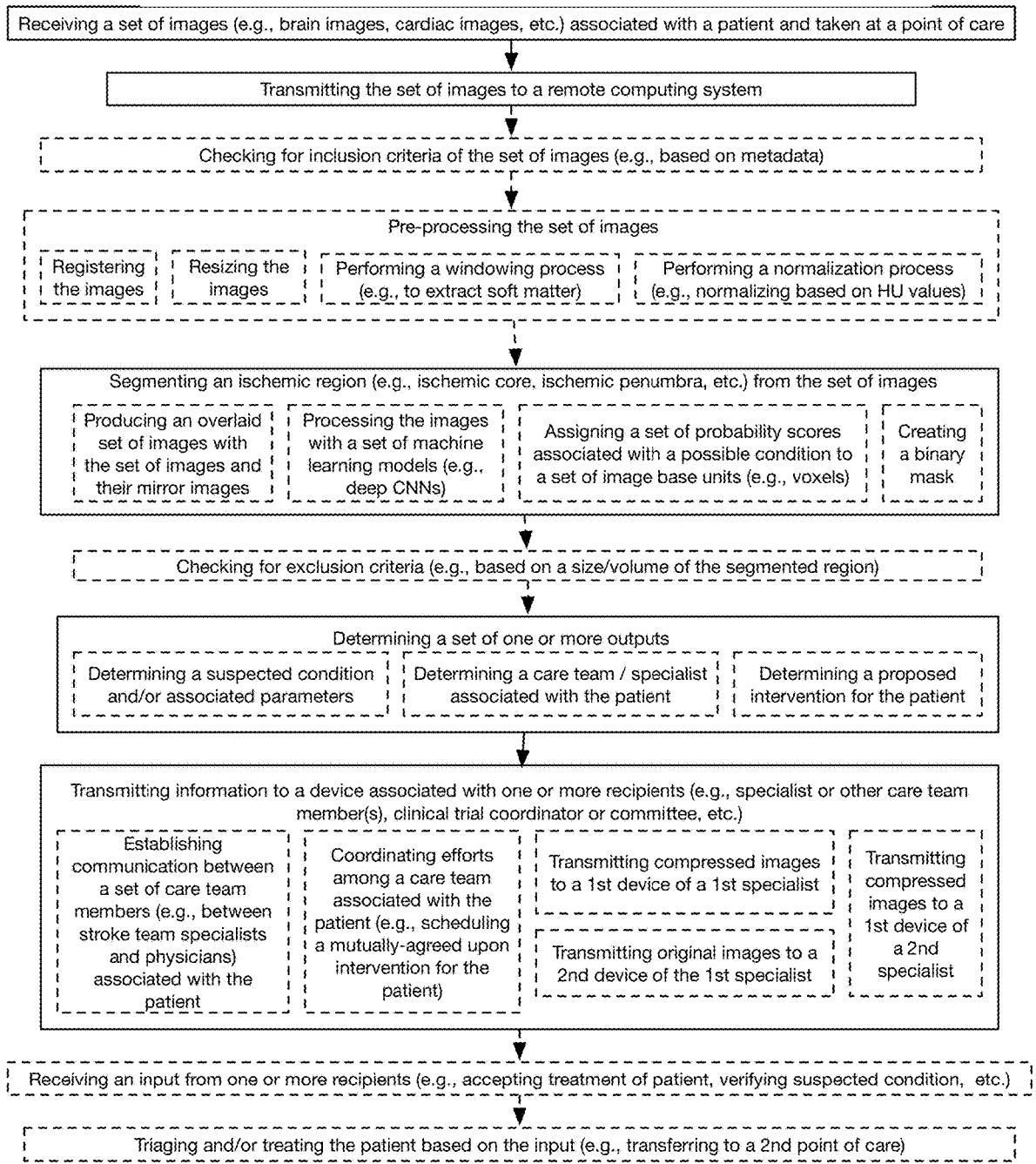
FIG. 8 depicts a variation of the method.

In a specific example (e.g., as shown in FIG. 7, as shown in FIG. 8), the method includes, at a remote computing system, receiving a set of brain images associated with the patient, wherein the set of brain images is concurrently sent to a standard radiology workflow operating in parallel with the method. In the standard radiology workflow, the radiologist analyzes the set of brain images and notifies a specialist based on a visual assessment of the set of brain images at the workstation, wherein the standard radiology workflow takes a first amount of time. The method can then include detecting an ischemic condition from the set of brain images, which includes any or all of: identifying an image dataset of a head from a brain scan; resizing each of the set of images; producing a mirror image of each of the set of images; superimposing the image with its mirror image; registering the image based on the superimposed image; detecting a potential ischemic core through a segmentation process using a deep CNN; providing a notification (e.g., through texting) to a specialist associated with a $2^{nd}$ point of care (e.g., different from the $1^{st}$ point of care, within the $1^{st}$ point of care, etc.); sending a compressed image dataset to the specialist; displaying a high resolution image dataset on a workstation of the specialist; and triggering an action based on input from the specialist (e.g., transfer of patient from the $1^{st}$ point of care to the $2^{nd}$ point of care, recommending the patient for a clinical trial, etc.). Within this variation and/or additionally or alternatively, the mirror image can be taken as an input after registration to the original image, wherein the original image is registered (e.g., straightened) based on its mirror image, wherein a registered mirror image of the registered image is then produced and used as an input.

In a second variation of the method 200, additional or alternative to the first, the method includes: at a remote computing system (e.g., remote from the first point of care), receiving a set of images (e.g., of a brain of the patient), automatically detecting a condition (e.g., ischemic core, early signs of ischemic core, etc.) from the set of images based on a deep learning model, determining a recipient (e.g., a specialist at a $1^{st}$ point of care, a specialist at a $2^{nd}$ point of care, a research coordinator of a clinical trial, etc.); notifying the recipient on a mobile device associated with the recipient; optionally displaying a compressed version of the set of images on the mobile device; and receiving an input from the recipient.

In a set of specific examples, the method further includes establishing communication (e.g., texting, call, HIPAA-compliant texting, HIPAA-compliant calling, etc.) between recipients, such as between any or all of: multiple healthcare workers (e.g., physicians, surgeons, etc.), multiple research coordinators (e.g., from the same clinical trial, from different clinical trials, etc.), a healthcare worker and a research coordinator (e.g., for the research coordinator to ask questions from the surgeon, as shown in FIG. 13, etc.), a research coordinator and a patient (e.g., to submit a consent form to the patient, to receive a consent form from the patient, etc.), a healthcare worker and a patient, and/or between any other suitable users and individuals.

Figure 9:
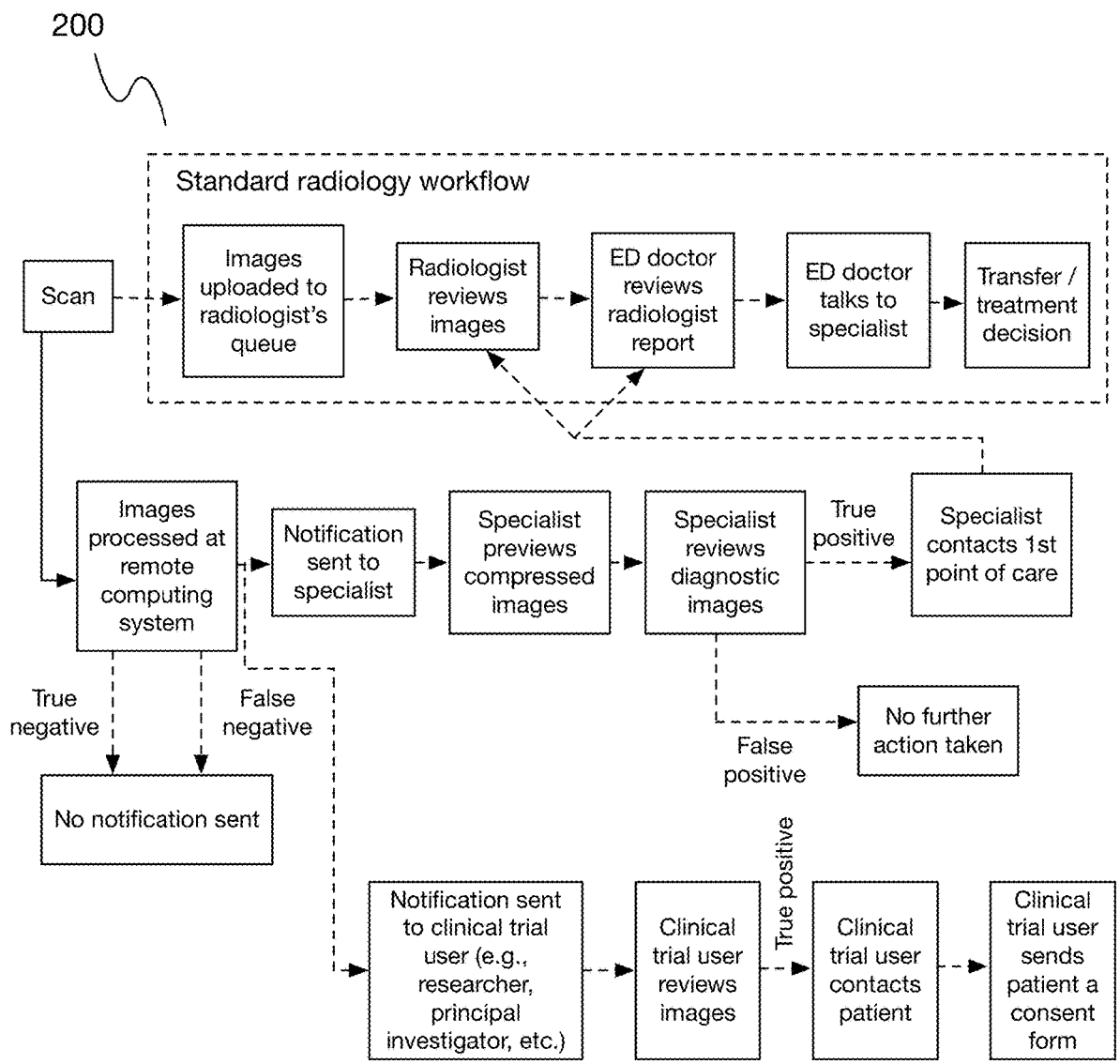
FIG. 9 depicts a variation of the method involving recommending the patient for a clinical trial.
Figure 11:
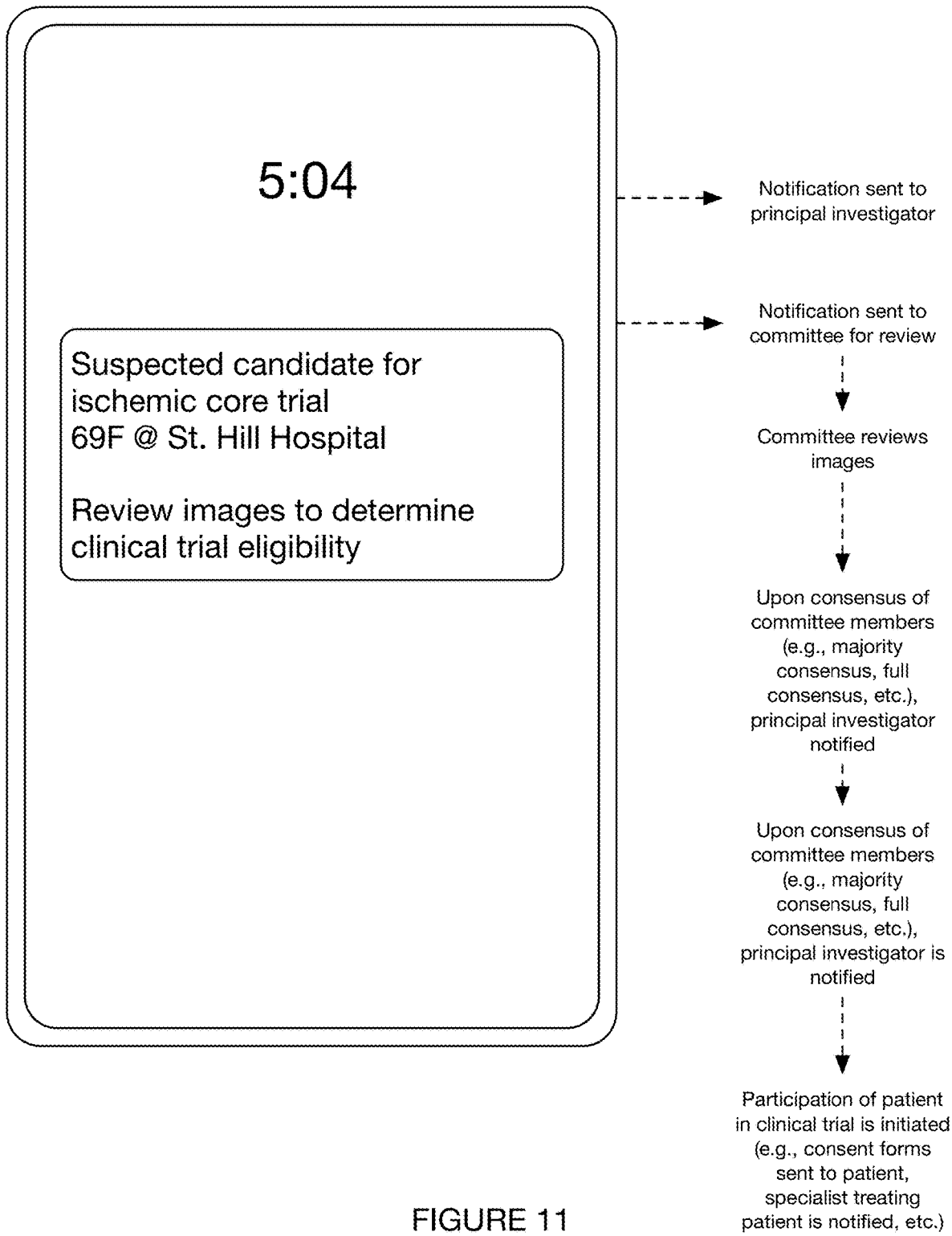
FIG. 11 depicts a variation of a notification and subsequent workflow of recommending a patient for a clinical trial.
Figure 12:
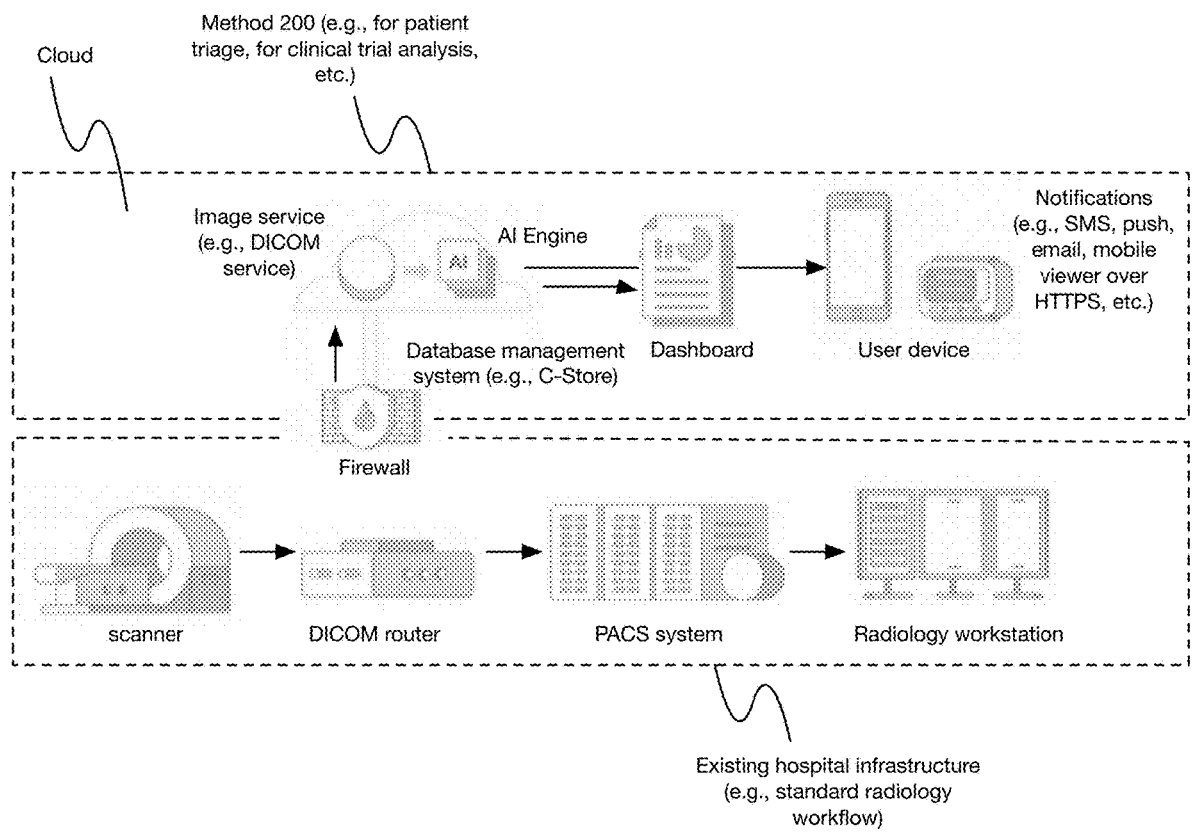
FIG. 12 depicts a variation of the system.

In a third variation of the method 200 (e.g., as shown in FIG. 9, as shown in FIG. 11, as performed in accordance with a system shown in FIG. 12, etc.), additional or alternative to those described above, the method functions to evaluate if a patient presenting with a potential pathology qualifies for a clinical trial and if so, to alert (e.g., automatically, in a time period shorter than a determination made by a radiologist in a standard radiology workflow, etc.) a research coordinator (e.g., principal investigator) associated with the clinical trial, wherein the method includes: receiving a data packet comprising a set of images (e.g., NCCT images of a brain of the patient) sampled at the first point of care, wherein the data packet is optionally concurrently sent to the standard radiology workflow; segmenting the images and comparing with set of clinical trial criteria (e.g., inclusion criteria, exclusion criteria, etc.); and in an event that the images satisfy the clinical trial criteria (e.g., according to a set of thresholds), presenting a notification on a mobile device associated with the research coordinator (e.g., as shown in FIG. 11). If the research coordinator decides to include the patient in the clinical trial (e.g., based on the notification, based on a set of compressed images sent to a user device of the research coordinator, based on a calculated parameter, based on a consensus reached by a clinical trial committee in communication with the research coordinator, etc.), the research coordinator or other user or entity can optionally transmit a consent form to the patient (e.g., to a user device of the patient, to a workstation associated with the $1^{st}$ point of care, to a workstation associated with the $2^{nd}$ point of care, etc.) and/or to a healthcare worker (e.g., to a user device of the healthcare worker, to a workstation of the healthcare worker, etc.), such as a surgeon, associated with the patient (e.g., via a client application executing on a user device of the research coordinator, from a remote computing system, etc.). Additionally or alternatively, the research coordinator can communicate (e.g., via a HIPAA-compliant messaging platform established through the client application, through a text messaging application, etc.) with a physician associated with the patient, and/or otherwise review and communicate information.

Additionally or alternatively, the method can include any or all of: providing a mobile image viewer at a client application with visible protected health information after secure login by the recipient; providing a patient status tracker to keep the recipient informed of updates to the patient; providing case volume information, which can detect and alert recipients about patients throughout the hub and spoke network that can benefit from a particular treatment (e.g., neurosurgical treatment); providing bed capacity information to a recipient, which enables increased access to early surgical intervention (e.g., thereby leading to improved patient outcomes, decreased hospital length of stay, decreased ventilator use, etc.); and/or any other processes.

Additionally or alternatively, the method can include any other steps performed in any suitable order.

Although omitted for conciseness, the preferred embodiments include every combination and permutation of the various system components and the various method processes, wherein the method processes can be performed in any suitable order, sequentially or concurrently.

As a person skilled in the art will recognize from the previous detailed description and from the figures and claims, modifications and changes can be made to the preferred embodiments of the invention without departing from the scope of this invention defined in the following claims.

We claim:

1. A method for automatically detecting a potential ischemic condition, the method comprising:
    at a computing system:
        receiving a first set of images associated with a patient and taken at a first point of care;
        processing the first set of images, wherein processing the set of images comprises:
            producing a mirror image version of each of the first set of images, thereby producing a mirrored set of images;
            overlaying and aligning the mirrored set of images with the first set of images, thereby producing an overlaid set of images;
            segmenting an ischemic region from the first set of images based on a set of deep learning models, wherein a set of inputs of the set of deep learning models comprises the first set of images and the set of overlaid images;
            automatically detecting the potential ischemic condition based on the segmented ischemic region;
            compressing the first set of images to produce a compressed set of images;
    in response to detecting the potential ischemic condition, automatically:
        determining, at the computing system, a specialist associated with a treatment of the potential ischemic condition;
        transmitting a notification and at least one image of the compressed set of images to a recipient, wherein the recipient is the specialist, at a client application executing on a user device associated with the specialist; and
    receiving an input from the specialist at the client application, wherein the input triggers an assignment of a treatment of the patient to the specialist.

2. The method of claim 1, wherein the specialist is associated with a second point of care remote from the first point of care.

3. The method of claim 1, further comprising determining a first image of the at least one image of the compressed set of images, wherein the first image is provided as a thumbnail with the notification.

4. The method of claim 3, wherein the first image corresponds to a maximum cross section of the ischemic region.

5. The method of claim 1, further comprising receiving a read receipt at the computing system upon the specialist opening the notification, wherein in an event that the read receipt is not received within a predetermined time threshold, the method further comprises transmitting the notification and the at least one image to a second specialist at a second user device associated with the second specialist.

6. The method of claim 1, further comprising checking for a set of inclusion criteria of the first set of images based on metadata associated with the first set of images.

7. The method of claim 1, further comprising, after detecting the potential ischemic condition, notifying a second recipient associated with the potential ischemic condition.

8. The method of claim 7, further comprising establishing communication between the first and second recipients.

9. The method of claim 8, wherein the second recipient is a principal investigator associated with a clinical trial.

10. The method of claim 1, further comprising implementing a buffering protocol, wherein the buffering protocol comprises transmitting a remainder of the compressed set of images to the first recipient at a set of times later than a first time at which the at least one image is transmitted.

11. The method of claim 1, wherein the set of images is concurrently sent to a standard radiology workflow at the first point of care, wherein the method at least partially overlaps with the standard radiology workflow.

12. A method for automatically detecting a potential ischemic condition, the method comprising:
at a computing system:
receiving a first set of images associated with a patient;
processing the first set of images with a deep learning model, wherein processing the first set of images comprises segmenting an ischemic region corresponding to the ischemic condition, and wherein a set of inputs of the deep learning model comprises the first set of images and a mirrored version of the first set of images;
in response to detecting the potential ischemic condition based on the segmented ischemic region, automatically:
determining, at the computing system, a recipient associated with the potential ischemic condition;
transmitting a notification and at least one image determined based on the first set of images to the recipient at a client application executing on a user device associated with the recipient;
receiving an input from the recipient at the client application.

13. The method of claim 12, wherein the ischemic condition is an ischemic core.

14. The method of claim 12, wherein the input triggers an assignment of a treatment of the patient to a care team associated with the recipient.

15. The method of claim 14, wherein the recipient is a specialist of the care team, wherein the care team is a stroke care team.

16. The method of claim 15, further comprising:
transmitting the notification and the at least one image to a second recipient at a second client application executing on a second user device associated with the second recipient, wherein the second recipient is part of the stroke care team; and
establishing a communication interface between the first and second client applications.

17. The method of claim 12, wherein the at least one image is a compressed version of an image of the first set of images.

18. The method of claim 12, wherein the recipient is a principal investigator associated with a clinical trial.

19. The method of claim 12, wherein a first image of the at least one image corresponds to a maximum cross section of the hyperdense region.

20. The method of claim 19, wherein the first image is provided as a thumbnail with the notification.

* * * * *